United States Patent [19]
Coe et al.

[11] Patent Number: 5,444,062
[45] Date of Patent: Aug. 22, 1995

[54] QUINAZOLINES DERIVATIVES FOR ENHANCING ANTITUMOR ACTIVITY

[75] Inventors: Jotham W. Coe, Mystic; Anton F. J. Fliri, Norwich; Takushi Kaneko, Guilford; Eric R. Larson, Mystic, all of Conn.

[73] Assignee: Pfizer Inc., New York, N.Y.

[21] Appl. No.: 50,047

[22] PCT Filed: Oct. 10, 1991

[86] PCT No.: PCT/US91/07254
§ 371 Date: May 5, 1993
§ 102(e) Date: May 5, 1993

Related U.S. Application Data

[63] Continuation of Ser. No. 609,986, Nov. 6, 1990, abandoned.

[51] Int. Cl.$^6$ .................. A61K 31/505; C07D 239/95
[52] U.S. Cl. ....................... 514/260; 514/267; 544/250; 544/291
[58] Field of Search ................ 544/250, 291; 514/260, 514/267

[56] References Cited

U.S. PATENT DOCUMENTS

| | | | |
|---|---|---|---|
| 3,511,836 | 5/1970 | Hess | 260/256.4 |
| 3,635,979 | 1/1972 | Hess | 260/256.4 |
| 3,956,495 | 5/1976 | Lacefield | 424/251 |
| 3,960,861 | 6/1976 | Danilewicz et al. | 544/284 |
| 4,098,788 | 7/1978 | Crenshaw | 544/293 |
| 5,064,833 | 11/1991 | Ife et al. | 514/260 |

FOREIGN PATENT DOCUMENTS

| | | |
|---|---|---|
| 028473 | of 1981 | European Pat. Off. . |
| 326329 | 8/1989 | European Pat. Off. . |
| 1310457 | 12/1959 | France . |
| 958197 | 2/1957 | Germany . |
| 457460 | 8/1968 | Switzerland . |
| 1390014 | of 1975 | United Kingdom . |
| 8905297 | of 1989 | WIPO . |

OTHER PUBLICATIONS

Postovski and Goncharova, Zh. Obshch. Khim., 32, 3323, 1962 with Chemical Abstracts 12555a.
Curd et. al., J. Chem. Soc., 775, 1947.
Millen, J. Med. Chem., 28, 12, 1985.
Richter et. al., J. Med. Chem., 17, 943, 1974.
Miki et. al., Chem. Pharm. Bul., 2813, 1982.
Safa et. al., Biochem. Biophys. Res. Comm., 166, 259, 1990.
Kaneko, T., Current Opinion in Therapeutic Patents, Jul. 1991.
Hochhauser, D. and Harris, A. L., Brit. Med. Bull., 47, 178–190 (1991).
Bellamy, W. T., Dalton, W. S. and Dorr, R. T., Cancer Invest, 8, 547–562 (1990).
Gottesman et al., J. Bio. Chem., vol. 263, No. 25, pp. 12163–12166, 1988.
Twentyman et al., Cancer Chemotherapy and Pharmacology (1991) 29: 24–28.
Sato et al., Cancer Research 51, 2420–2424, May 1, 1991.
Sonneveld et al., The Lancet, vol. 340, No. 8814, 255–259, 1992.
Tsuruo, T., Xenobiotics and Cancer, L. Ernster et al. (Eds), Japan Sci. Soc. Press, Tokyo/Taylor & Francis Ltd., London, pp. 241–251, 1991.
Fojo et al., Cancer Research, 45, 3002–3007, Jun. 1985.
Boesch, D. et al., Cancer Research, 51, 4226–4233, Aug. 15, 1991.
Naito, M. et al., Cancer Chemotherapy and Pharmacology, (1992) 29: 195–200.

*Primary Examiner*—Mukund J. Shah
*Assistant Examiner*—Matthew V. Grumbling
*Attorney, Agent, or Firm*—Peter C. Richardson; Benson Gregg C.

[57] ABSTRACT

2,4-Diaminoquinazoline derivatives as potentiators of chemotherapeutic agents in the treatment of cancer.

27 Claims, No Drawings

QUINAZOLINES DERIVATIVES FOR ENHANCING ANTITUMOR ACTIVITY

CROSS REFERENCE TO RELATED APPLICATIONS

This application is the national stage of International Application No. PCT/US91/07254, filed Oct. 10, 1991, designating, inter alia, the United States which is a continuation of U.S. Ser. No. 07/609,986, filed Nov. 6, 1990, now abandoned.

BACKGROUND OF THE INVENTION

This invention relates to 2,4-diaminoquinazolines and their use as sensitizers of tumor cells to anticancer cells.

In cancer chemotherapy the effectiveness of anticancer drugs is often limited by the resistance of tumor cells. Some tumors such as of the colon, pancreas, kidney and liver are generally innately resistant, and other responding tumors often develop resistance during the course of chemotherapy. The phenomena of multidrug resistance (MDR) is characterized by the tumor cell's cross-resistance to structurally unrelated drugs. The drugs which are the target of resistance include adriamycin, daunomycin, vinblastine, vincristine, actinomycin D and etoposide. The resistance cells are often associated with over-expression of the mdrl gene. This gene product is a family of 140–220 kd trans-membrane phosphoglycoprotein (P-glycoprotein) which functions as an ATP-dependent efflux pump. Thus, it has been postulated that this efflux mechanism keeps the intracellular level of the anticancer drug low, allowing the tumor cells to survive.

In recent years various substances such as verapamil, nifedipine and diltiazem have been used in in vitro experimental systems to reverse the MDR phenomena. More recently some of these agents have been tested clinically as MDR reversing agents. Little efficacy has been observed with verapamil or trifluoroperazine. Thus, there is a need for an effective MDR reversing agent.

The 2,4-diaminoquinazolines are prepared by known methods utilizing 2,4-dichloroquinazolines [Postovskii and Goncharova, *Zh. Obsch. Khim.*, 32, 3323 (1962)]. Curd et al. (*J. Chem. Soc.*, 1947, 775) reported the synthesis of 2,4-dichloroquinazolines from the corresponding 2,4(1H, 3H)quinazolinedione. The Wellcome Foundation discloses 2,4-diaminoquinazolines of general structure D as antibacterials [GB patent 806772 (1958)]. Hess [U.S. Pat. No. 3,511,836 (1970)] patented compounds of structures E, F, and G as antihypertensive agents. Wijbe [GB patent 1,390,014 (1975)] patented a process for compounds of structure H and these compounds are claimed to be antibacterials. Lacefield [U.S. Pat. No. 3,956,495 (1976)] describes compounds of the general formula I as antithrombotic agents. Crenshaw [U.S. Pat. No. 4,098,788 (1978)] patented a process for the production of compounds of formula J. Hess [European Patent 0,028,473 (1981)] describes chloro- and alkoxy-substituted 2,4-diaminoquinazolines of formula K. Ife et al. describe compounds of general structur L as inhibitors of gastric acid secretion [WO 89/0527 (1989)]. Compounds of structures M and N were published as phosphodiesterase inhibitors [Miller, *J. Med. Chem.*, 28, 12 (1985)]. Richter et al. published compounds of structur O as inhibitors of dihydrofolate reductase [*J. Med. Chem.*, 17, 943 (1974)]. In search of compounds with herbicidal activity Miki et al. reported the synthesis of 2,4-dialkglaminoquinazolines (P) (*Chem. Pharm. Bull.* 30, 2313 (1982)]. Arylazidoprazosin (Q) has been shown to bind to P-glycoprotein [Safa et al., *Biochem. Biophys. Res. Comm.* 166, 259 (1990)].

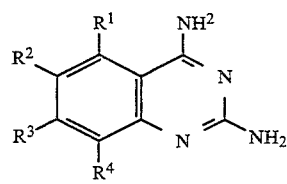

D

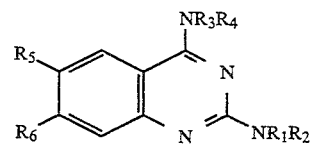

E

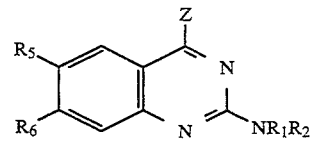

F

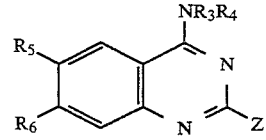

G

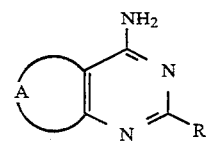

H

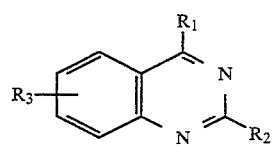

I

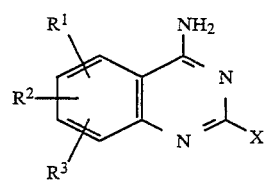

J

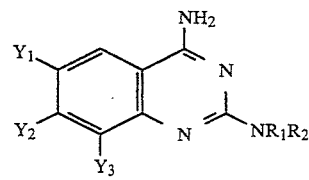

K

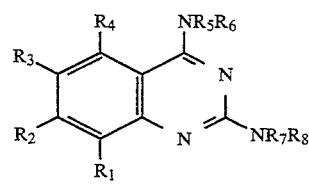

L

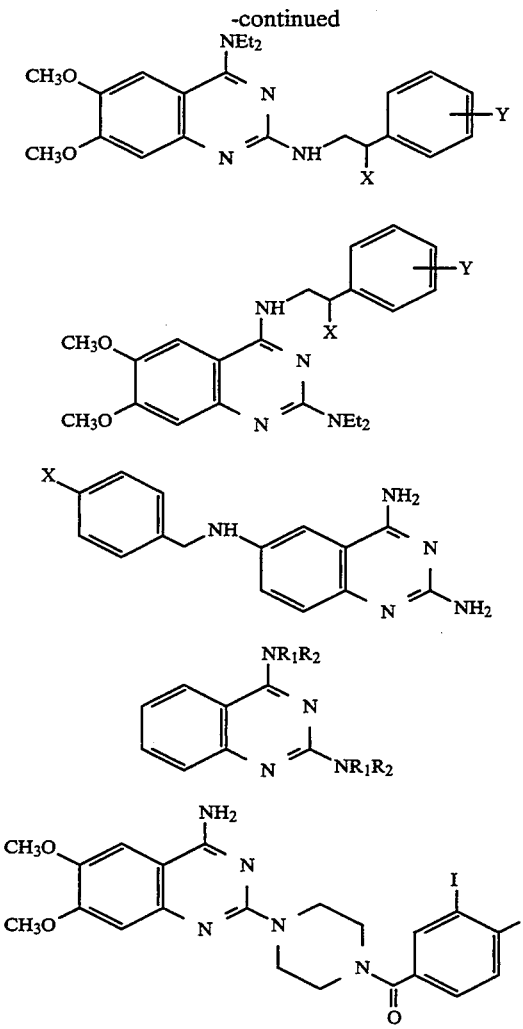

four carbon atoms; X and $X^1$ together are ethylenedioxy or methylenedioxy; $R_1$ is alkyl having one to four carbon atoms, cycloalkyl of three to seven carbon atoms, alkoxyalkyl said alkoxy having one to three carbon atoms and said alkyl having two to three carbon atoms or benzodioxan-2-ylmethyl; $R_2$ is hydrogen, alkyl of one to eight carbon atoms or benzyl; $R_1$ and $R_2$ when taken together with the nitrogen atom to which they are attached form (a) a moiety of the formula

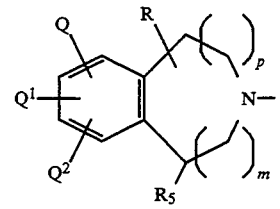

where Q is hydrogen, alkoxy of one to three carbon atoms, hydroxy, alkanoylamino having two to four carbon atoms, alkyl of one to three carbon atoms, bromo, iodo, chloro, fluoro, nitro, morpholino, amino, alkylamino of one to three carbon atoms or dialkylamino of two to six carbon atoms, $Q^1$ is hydrogen, fluoro, chloro, bromo, alkyl having one to three carbon atoms or alkoxy having one to three carbon atoms, $Q^2$ is hydrogen or alkoxy of one to three carbon atoms, $Q^1$ and $Q^2$ together are methylenedioxy or ethylenedioxy, R is hydrogen, alkyl having one to four carbon atoms or alkoxy of one to three carbon atoms, m is an integer of 0–2, p is an integer of 1–2, $R_5$ is hydrogen or dialkoxybenzyl said alkoxy having one to three carbon atoms and R and $R_5$ together are alkylene having one to three carbon atoms, (b) 1,2,3,4-tetrahydro-beta-carbolin-2-yl or
(c) piperidino of the formula

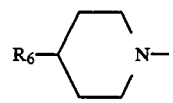

where $R_4$ is pyridylmethoxy, alkoxyalkyleneoxy said alkoxy having one to three carbon atoms and said alkylene having two to three carbon atoms or benzoxazol-2-ylmethyl (d) octahydroisoindol-2-yl or
(e) decahydroisoquinol-2-yl;
$R_3$ is
(a) cycloalkyl of three to seven carbon atoms,
(b) benzodioxan-2-ylmethyl
(c) arylalkyl of the formula

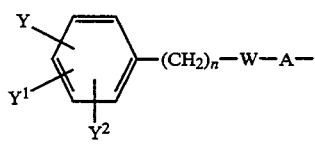

wherein n is an integer of 1 or 0, W is O, S or a chemical bond, A is alkylene of one to four carbon atoms, Y is hydrogen, alkyl of one to three carbon atoms, fluoro, chloro, bromo, hydroxy, alkoxy of

SUMMARY OF THE INVENTION

The compound of the present invention are of the formula

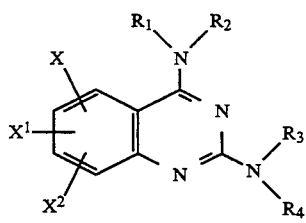

or a pharmaceutically acceptable acid addition salt thereof where X and $X^1$ are each hydrogen, alkyl of one to four carbon atoms, iodo, bromo, nitro, chloro, fluoro, methylthio, amino, alkylamino of one to three carbon atoms, methylsulfinyl, aminomethyl, $(CH_3)_2S^\oplus$, dialkylaminomethyl of three to seven carbon atoms, hydroxymethyl, morpholino, thiomorpholino, benzoylamino, substituted benzoylamino wherein said substituent is azido, methoxy, methyl, fluoro, chloro, or trifluoromethyl, alkanoylamino having two to four carbon atoms, 4-methylpiperazino, piperazino, piperidino, pyrrolidino, dialkylamino of two to six carbon atoms or alkoxy of one to four carbon atoms; $X^2$ is hydrogen, alkyl of one to four carbon atoms or alkoxy of one to one to three carbon atoms, benzyloxy, nitro, dimethylamino or amino, $Y^1$ is hydrogen, alkoxy of one to three carbon atoms, chloro, fluoro, hydroxy or benzyloxy, $Y^2$ is hydrogen or alkoxy of one to three carbon atoms and Y and $Y^1$ together are methylenedioxy or ethylenedioxy, (d) arylalkyl of the formula

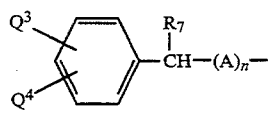

where $R_7$ is hydrogen, alkoxy of one to three carbon atoms or $C_4H_5(CH_2)_1O$, n is 1, t is an integer of 1 or 0, A is alkylene of one to four carbon atoms, $Q^3$ and $Q^4$ are each hydrogen or alkoxy of one to three carbon atoms and $Q^3$ and $Q^4$ together are methylenedioxy or ethylenedioxy, (e) pyridylalkyl said alkyl having one to four carbon atoms, (f) alkoxyalkyl said alkoxy having one to three carbon atoms and said alkyl having two to three carbon atoms, (g) indolylalkyl of the formula

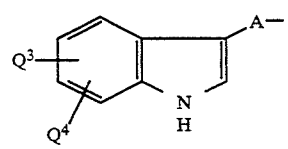

where A is alkylene of one to four carbon atoms, $Q^3$ and $Q^4$ are each hydrogen or alkoxy of one to three carbon atoms and $Q^3$ and $Q^4$ together are ethylenedioxy of methylenedioxy, (h) tetrahydronaphthalyl of the formula

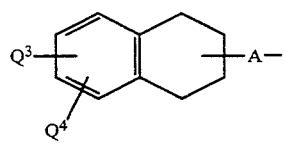

wherein A is alkylene of one to four carbon atoms, $Q^3$ and $Q^4$ are each hydrogen or alkoxy of one to three carbon atoms and $Q^3$ and $Q^4$ together are ethylenedioxy or methylenedioxy;

(i) arylalkanol of the formula

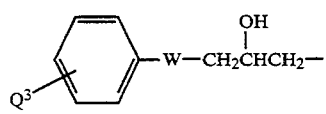

where W is O, S or a chemical bond and $Q^3$ is hydrogen or alkoxy of one to three carbon atoms, (j) 2,3-dihydro-2-hydroxyinden-1-yl, (k) arylcycloalkyl of the formula

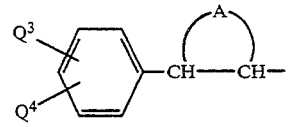

wherein A is alkylene having one to four carbon atoms, $Q^3$ and $Q^4$ are each hydrogen or alkoxy having one to three carbon atoms and $Q^3$ and $Q^4$ together are ethylenedioxy or methylenedioxy, (l) indene of the formula

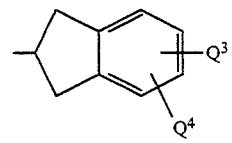

wherein $Q^3$ and $Q^4$ are each hydrogen or alkoxy of one to three carbon atoms and $Q^3$ and $Q^4$ together are ethylenedioxy or methylenedioxy, (m) naphthyl or (n) 1-methylpyrrol-2-yl;

$R_4$ is hydrogen or alkyl of one to eight carbon atoms and $R_3$ and $R_4$ taken together with the nitrogen atom to which they are attached form (a) a tetrahydroisoquinolinyl of the formula

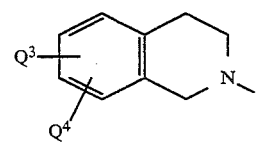

where $Q^3$ and $Q^4$ are each hydrogen or alkoxy of one to three carbon atoms and $Q^3$ and $Q^4$ together are methylenedioxy or ethylenedioxy, (b) piperidino of the formula

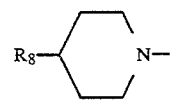

wherein $R_4$ is benzyl, alkoxyalkyleneoxy said alkoxy having from one to three carbon atoms and said alkylene having two to three carbon atoms or alkyl sulfonamide of the formula

where $R_9$ is alkyl of one to four carbon atoms (c) 3-methyl-3-phenylpiperidino or (d) piperazino of the formula

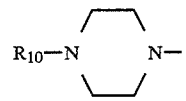

where $R_{10}$ is hydrogen, alkoxycarbonyl of two to six carbon atoms, acyl of one to six carbon atoms, hydroxyalkoxycarbonyl of three to six carbon atoms, furoyl, benzoxazol-2-yl, pyrimid-2-yl or benzodioxan-2-ylcarbonyl; provided that:

when X and $X^1$ are each hydrogen, alkyl having one to four carbon atoms, alkoxy having one to four carbon atoms, bromo, iodo, amino, alkylamino having one to three carbon atoms, methylthio, dialkylamino having two to six carbon atoms, fluoro or chloro; $X^2$ is hydrogen, alkyl having one to four carbon atoms or alkoxy having one to four carbon atoms; $R_1$ is alkyl having one to four carbon atoms; $R_2$ is hydrogen or alkyl having one to four carbon atoms; $R_3$ is

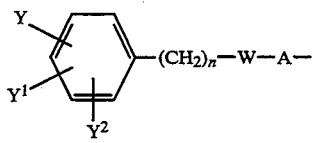

wherein W is a chemical bond, n is 1 and A is alkylene having one to three carbon atoms or W is a chemical bond, n is 0 and A is alkylene having one to four carbon atoms; Y is hydrogen, alkyl having one to three carbon atoms, alkoxy having one to three carbon atoms, fluoro, chloro, bromo hydroxy or amino; $Y^1$ is hydrogen, alkoxy having one to three carbon atoms, chloro, fluoro or hydroxy; $Y^2$ is hydrogen or alkoxy having one to three carbon atoms, $R^4$ cannot be hydrogen or alkyl having one to four carbon atoms.

A preferred group of compounds are those where X and $X^1$ are each alkoxy of one to four carbon atoms, $X^2$ is hydrogen, $R_1$ and $R_2$ when taken together with the nitrogen atom to which they are attached form a moiety of the formula

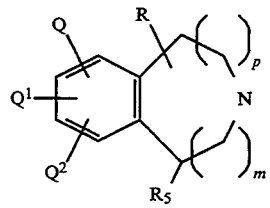

where $Q^1$ is alkoxy of one to three carbon atoms, R and $R_5$ are each hydrogen, p is 1, m is 0, $R_3$ is arylalkyl of the formula

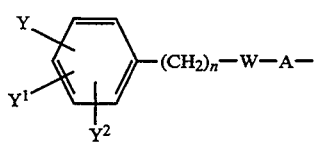

where $Y^1$ and $Y^2$ are each methoxy, n is 0, W is a chemical bond, A is ethylene and $R_4$ is hydrogen. Especially preferred within this group are the compounds where X is 6-methoxy, $X^1$ is 7-methoxy, Q is 5-hydroxy, $Q^1$ is 6-methoxy, $Q^2$ is hydrogen, Y is hydrogen, $Y^1$ is 2-methoxy and $Y^2$ is 3-methoxy, where X is 6-methoxy, $X^1$ is 7-methoxy, Q is 6-methoxy, $Q^1$ is 7-methoxy, $Q^2$ is hydrogen, Y is hydrogen, $Y^1$ is 3-methoxy and $Y^2$ is 4-methoxy, where X is 6-methoxy, $X^1$ is 7-methoxy, Q is 7-methoxy, $Q^1$ is 8-methoxy, $Q^2$ is hydrogen, Y is hydrogen, $Y^1$ is 2-methoxy and $Y^2$ is 3-methoxy, where X is 6-methoxy, $X^1$ is 7-methoxy, Q and $Q^2$ are each hydrogen, $Q^1$ is 6-methoxy, Y is hydrogen, $Y^1$ is 3-methoxy and $Y^2$ is 4-methoxy, where X is 6-methoxy, $X^1$ is 7-methoxy, Q is 5-methoxy, $Q^1$ is 6-methoxy, $Q^2$ is hydrogen, Y is hydrogen, $Y^1$ is 3-methoxy and $Y^2$ is 4-methoxy, where X is 6-methoxy, $X^1$ is 7-methoxy, Q is 6-methoxy, $Q^1$ is 7-methoxy, $Q^3$ is hydrogen, Y is 2-bromo, $Y^1$ is 4-methoxy and $Y^2$ is 5-methoxy, where X is 6-methoxy, $X^1$ is 7-methoxy, Q is 6-methoxy, $Q^1$ is 8-methoxy, $Q^2$ is hydrogen, Y is hydrogen, $Y^1$ is 3-methoxy and $Y^2$ is 4-methoxy and where X is 6-methoxy, $X^1$ is 7-methoxy, Q is 7-methoxy, $Q^1$ is 8-methoxy, $Q^3$ is hydrogen, Y is hydrogen, $Y^1$ is 3-methoxy and $Y^2$ is 4-methoxy.

A second group of preferred compounds are those where $X^1$ and $X^2$ are each hydrogen, $R_1$ and $R_2$ when taken together with the nitrogen atom to which they are attached form a moiety of the formula

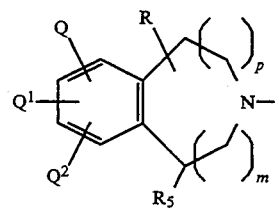

where Q and $Q^1$ are each alkoxy of one to three carbon atoms, $Q^2$ is hydrogen, R and $R_5$ are each hydrogen, p is 1, m is 0, $R_3$ is arylaklyl of the formula

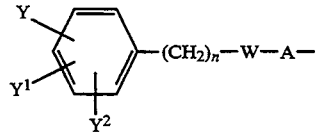

wherein $Y^2$ is hydrogen, n is 0, W is a chemical bond and A is ethylene and $R_4$ is hydrogen. Especially preferred within this group are compound where X is 5-methoxy, Q is 6-methoxy, $Q^1$ is 7-methoxy, Y is 2-chloro and $Y^1$ is hydrogen, where X is 5-chloro, Q is 6-methoxy, $Q^1$ is 7-methoxy, Y is 2-chloro and $Y^1$ is hydrogen, where X is 5-methyl, Q is 6-methoxy, $Q^1$ is 7-methoxy, Y is 3-methoxy and $Y^1$ is 4-methoxy and where X is 6-dimethylamino, Q is 6-methoxy, $Q^1$ is 7-methoxy, Y is 3-methoxy and $Y^1$ is 4-methoxy.

A third group of preferred compounds are those where X and $X^1$ are each alkoxy of one to four carbon atoms, $X^2$ is hydrogen, $R_1$ and $R_2$ when taken together with the nitrogen atom to which they are attached form a moiety of the formula

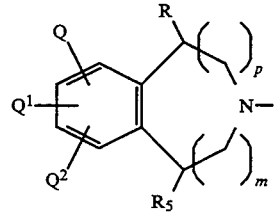

wherein $Q^2$ is hydrogen, $R_5$ is hydrogen, p is 1-2, $R_5$ is arylalkyl of the formula

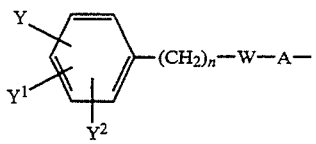

where Y and $Y^1$ are each alkoxy of one to three carbon atoms, $Y^2$ is hydrogen, n is O, N is a chemical bond, A is ethylene and $R_4$ is hydrogen. Especially preferred within this group are compounds where X is 6-methoxy, $X^1$ is 7-methoxy, Q and $Q^1$ are each hydrogen, p is 1, R is methoxy, m is 0, Y is 2-methoxy and $Y^1$ is 3-methoxy, where X is 6-methoxy, $X^1$ is 7-methoxy, Q and $Q^1$ are each hydrogen, p is 2, R is hydrogen, m is 1, Y is 3-methoxy and $Y^1$ is 4-methoxy and where X is 6-methoxy, $X^1$ is 7-methoxy, Q is 7-amino, $Q^1$ is hydrogen, R is methoxy, m is 0, p is 1, Y is 3-methoxy and $Y^1$ is 4-methoxy.

A fourth group of preferred compounds those where X and $X^1$ are each alkoxy of one to four carbon atoms, $R_1$ and $R_2$ when taken together with the nitrogen atom to which they are attached form a moiety of the formula

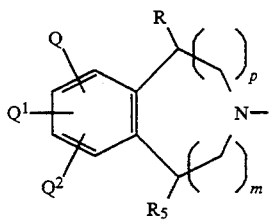

where Q and $Q^1$ are each alkoxy of one to three carbon atoms, $Q^2$ is hydrogen, R and $R_5$ are each hydrogen, p is 1, m is 0, $R_3$ is arylalkyl of the formula

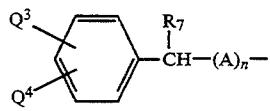

where $Q^3$ and $Q^4$ are each alkoxy of one to three carbon atoms, $R_7$ is methoxy, n is 1, A is methylene and $R_4$ is hydrogen. Especially preferred within this group is the compound where X is 6-methoxy, $X^1$ is 7-methoxy, Q is 6-fluoro, R is methoxy, $Q^3$ is 2-methoxy and $Q^4$ is 3-methoxy.

A fifth group of preferred compounds are those where $X^1$ is alkoxy of one to four carbon atoms, $X^2$ is hydrogen, $R_1$ and $R_2$ when taken together with the nitrogen atom to which they are attached form a moiety of the formula

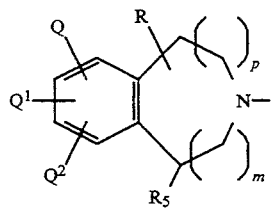

where Q and $Q^1$ are each alkoxy of one to three carbon atoms, $Q^2$ is hydrogen, p is 1, m is 0, $R_3$ is arylalkyl of the formula

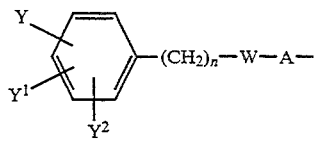

where $Y^2$ is hydrogen, n is 0, W is a chemical bond, A is ethylene and $R_4$ is hydrogen. Especially preferred within this group is the compound where X is 6-chloro, $X^1$ is 7-methoxy, Q is 6-methoxy, $Q^1$ is 7-methoxy, R and $R_5$ are each hydrogen, Y is 3-methoxy and $Y^1$ is 4-methoxy.

The present invention also includes a method of inhibiting a P-glycoprotein in a mammal in need of such treatment which comprises administering to said mammal a P-glycoprotein inhibiting amount of a compound of formula I. Preferred is the method where the mammal is a human suffering from cancer and said compound is administered before, with or after the administration to said human of an anticancer effective amount of a chemotherapeutic agent.

Also included is a pharmaceutical composition for administration to a mammal which comprises a P-glycoprotein inhibiting amount of a compound of formula I, a pharmaceutically acceptable carrier and, optionally, an anticancer effective amount of a chemotherapeutic agent.

As previously indicated, the compounds of formula I form pharmaceutically acceptable acid addition salts. Said pharmaceutically acceptable acid addition salts include, but are not limited to, those with HCl, HBr, $HNO_3$, $H_2SO_4$, $H_3PO_4$, $CH_3SO_3H$, p—$CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual mono-acid addition salt.

As one skilled in the art recognized, compounds of formula I have the potential for containing asymmetric carbon atoms. All these potential isomers are considered within the scope of the present invention.

The terms "alkyl" and "alkylene" are meant to embrace both straight chained and branched members.

DETAILED DESCRIPTION OF THE INVENTION

Compounds of the present invention are prepared with the reaction of a 2,4-dichloroquinazoline with an equivalent of an appropriate amine, $R_1R_2NH$, followed by the reaction of the product, a 2-chloro-4-aminoquinazoline derivative, with a second equivalent of an appropriate amine, $R_3R_4NH$.

In a more detailed description of the procedure, one molar equivalent of an optionally substituted 2,4-dichloroquinazoline and one molar equivalent of a tertiary amine-acid scavenger, such as triethylamine, N-methylmorpholine or diethylisopropylamine and one molar equivalent of an amine, $R_1R_2NH$, are combined in an anhydrous solvent such as dimethylacetamide, dioxane or N-methyl-2-pyrrolidone and maintained at from 0° C. to about 25° C. for a period of 1 to 48 hours.

The reaction mixture can be filtered and the filtrate concentrated to dryness in vacuo, or the reaction mixture can be quenched in water and the intermediate product either filtered or extracted with a water immiscible solvent such as methylene chloride or ethyl acetate. Removal of the extracting solvent provides the desired product. Frequently, the residual can be induced to crystallize by trituration with an organic solvent, and further purified by recrystallization or column chromatography.

The second step of the sequence leading to the products of the present invention consists of combining one molar equivalent of the appropriate 2-chloro-4-aminoquinazoline with either two molar equivalents of an amine, $R_3R_4NH$, or one equivalent of said amine and one equivalent of a tertiary amine-acid scavenger as described above in a reaction-inert solvent such as ethoxyethoxyethanol, butanol, amyl alcohol or cyclohexanol for a period of 5 minutes to several hours at reaction temperatures of 100°–200° C.

The reaction mixture can be cooled to room temperature and treated with a 1-N solution of an appropriate acid, such as hydrochloric acid to give a precipitate of the desired product as the hydrochloride salt. Other acids would give the corresponding acid addition salt. In instances where the acid addition salt does not precipitate the free base product can be isolated by chromatographing the crude material on silica gel using an eluant such as chloroform, ethyl acetate, diethyl ether, methanol methylene chloride, ethanol or mixtures thereof and subsequently converted to the acid addition salt product. The products are isolated by removing the eluting solvents in vacuo. Purification of the product can be done by recrystallization.

Generation of the free base from an acid addition salt can readily be carried out by treating an aqueous solution or suspension of the salt with at least one equivalent of an organic or inorganic base followed by extraction of the free base product with a water immiscible solvent such as ethyl acetate or methylene chloride. Removal of the solvent gives the desired base.

Compounds of formula I are inhibitors of the functions of P-glycoprotein, particularly human mdr 1 protein or P-glycoprotein related and membrane associate proteins which are participating in the transport of xenobiotics or proteins across membranes e.g., cell membranes of eukariotic and proeukariotic origin e.g., pmfdr, however not exclusive or restricted to these examples.

Compounds enclosed in general formula I are useful in combination chemotherapy of cancer, malaria, viral infections such as AIDS, in therapy of septic shock syndrome or inflammation and may be useful in enhancing the tissue penetration of drugs where the penetration of these xenobiotics is limited due to the presence of P-glycoprotein or P-glycoprotein related functional proteins. Compounds of formula I increase the activity/efficacy of adriamycin, daunomycin, etoposide, epipodophyllotoxin congoners, actinomycin D, emetin, vincristin, vinblastin, chloroquine, antracyclin antibiotics and of drugs which are structurally and functionally related to the above mentioned examples, in particular when the activity of these drugs has been shown to be limited due to the presence and function of P-glycoprotein, e.g. human mdr 1 protein or P-glycoprotein related proteins.

The compounds of the present invention are evaluated as potentiators of chemotherapeutic agents using a Cellular Drug Retention Assay. This assay was designed to study the effect of compounds on cellular retention of radiolabled drug. In this case 14C-adriamycin retention by multidrug resistant human carcinoma cells, KBV1, is measured.

KBV1 cells are routinely grown in tissue culture as monolayers in DMEM high glucose medium containing 1 ug/ml vinblastine 10% heat inactivated fetal calf serum and supplemented with Glutamine, Pen-Strep and Garamycin.

The assay protocol (described below) should be applicable, with minor modifications, to a wide variety of cell lines grown in tissue culture.

Assay Protocol:

(1) Seed replicate 6-well tissue culture plates with $1.2 \times 10E6$ cells per 2 ml per well in absence of Vinblastine;

(2) Incubate 24 hrs at 37 degrees in humidified incubator (5% CO2);

(3) Aspirate off the spent media and overlay monolayers with 2 ml/well of fresh medium that is 2 uM in Adriamycin (2 uM unlabeled Adriamycin + 20000 cpm of 14C-Adr) and the test agent at concentrations varying from 0 to 100 uM;

(4) Following incubation for 3 hours at 37 degrees in humidified incubator, remove media and wash monolayers twice with 2 ml of ice-cold buffered saline;

(5) Detach monolayers using 0.5 ml of trypsin/EDTA, collect detached cells and transfer to scintillation vial. Rinse wells once with 0.5 ml of buffered saline and add to same vial containing cells;

(6) Add 5 ml of Beckman Ready-Safe scintillation fluid to vial, vortex and determine radioactivity per sample using a scintillation counter (10 minutes per sample);

(7) For background control: pre-incubate monolayers at 4 degrees for 15 minutes then remove media and add fresh ice-cold media containing Adr (see step 3). Following incubation for 3 hours at 4 degrees remove media and wash monolayers twice with 2 ml ice-cold buffered saline, then proceed as in step 5;

(8) Results are expressed as T/C and ED3× values as defined below:

T/C = pmoles Adr per 10E6 cells treated with test agent/pmoles Adr per 10E6 untreated cells ED3× = concentration of test agent that produces a 3 fold increase in cellular accumulation of radiolabeled Adr, i.e. T/C=3.

Calculations:

Specific cpm = [sample cpm—background cpm]
Specific activity = [cpm/total conc. of Adr]
pmoles Adr = [specific cpm/specific activity]
pmoles Adr per 10E6 cells = [(pmoles Adr per well/number of cells per well) × 10E6 cells]

As previously mentioned compounds of the present invention and salts thereof are useful in potentiating the anticancer effects of chemotherapeutic agents. Such agents can include adriamycin, daunomycin, aclacinomycin A, actinomycin C, antinomycin D, mithramycin, toyomycin, vinblastine, maytansine, bruceantin, homoharintonin, anguindin, neocarcinostatin, mitomycin C and anthramycin.

The compounds of the present invention can be administered with, 24 hours before or up to 72 hours after the administration of the chemotherapeutic agents. When administered with said agents, they can be taken either separately or coadministered in the same formulation.

The compounds of the present invention whether taken separately or in combination with an anti-cancer agent, are generally administered in the form of pharmaceutical compositions comprising at least one of the compounds of formula I and optionally a chemotherapeutic agent, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like, and, for parenteral administration, in the form of injectable solutions or suspensions, and the like.

For use in the potentiation of anti-cancer agents in a mammal, including man, a compound of formula I is given in an amount of about 0.5–100 mg/kg/day, in single or divided doses. A more preferred dosage range is 2–50 mg/kg/day, although in particular cases, at the discretion of the attending physician, doses outside the broader range may be required. The preferred route of administration is generally oral, but parenteral administration (e.g. intramuscular, intravenous, intradermal) will be preferred in special cases, e.g., where oral absorption is impaired as by disease, or where the patient is unable to swallow.

The present invention is illustrated by the following examples, but is not limited to the details or scope thereof.

EXAMPLE 1

2-(N-Methyl-3,4-dimethoxyphenethylamino)-4-(1,2,3,4-tetrahydro-6,7-dimethoxyisoquinol-2-yl)-6,7-dimethoxyquinazoline hydrochloride (I: $X=6\text{-}CH_3O$; $X^1=7\text{-}CH_3O$; $X^2=H$; $R_1R_2N=6,7\text{-}(CH_3O)_2\text{-}1,2,3,4\text{-}tetrahydroisoquinol\text{-}2\text{-}yl$; $R_3=3,4(CH_3O)_2phenethyl$; and $R_4=CH_3$)

A.
2-chloro-4-(1,2,3,4-tetrahydro-6,7-dimethoxyisoquinol-2yl)-6,7-dimethoxyquinazoline To 26.59 g of 2,4-dichloro-6,7-dimethoxyquinazoline and 20.39 g of triethylamine in 250 ml of warm dimethylacetamide was added to 23.1 g of 1,2,3,4-tetrahydro-6,7-dimethoxyisoquinoline in 300 ml of dry dimethylacetamide and the reaction mixture stirred at room temperatures under exclusion of moisture for 16 hours. The precipitate was filtered and the filtrate concentrated to dryness under reduced pressure. The residual product was recrystallized from methanol, 40.6 g, m.p. 183°–186° C.

B.
2-(N-methyl-3,4-dimethoxyphenethylamino)-4-(1,2,3,4-tetrahydro-6,7-dimethoxyisoquinol-2-yl)-6,7-dimethoxyquinazoline hydrochloride A mixture of 840 mg of the product of Example 1A and 1.28 g of N-methyl-3,4-dimethoxyphenethylamine in 1 ml of ethoxyethoxyethanol was stirred under an inert atmosphere for 1 hour at 150° C. The reaction mixture was cooled to room temperature and passed through a column packed with 30 g of silica gel under 2.5 atmosphere of nitrogen pressure with 500 ml of chloroform. The product was eluted with 2% (V:V) methanol in chloroform. The fraction containing the product (Rf 0.47 10% methanol in chloroform on silica) was concentrated in vacuo and the crude residue crystallized from 1N hydrochloric acid in methanol-water (1:1, V:V), 271 mg, m.p. 190°–192° C., $M^+=575.40$.

EXAMPLES 2–71

Employing the procedure of Example 1 and starting with the appropriate starting reagents, the following compounds were prepared as their hydrochloride salt unless otherwise indicated:

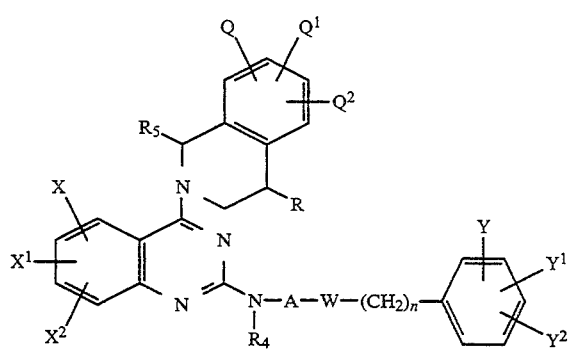

Example 2: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$ and $Y^2=H$; m.p. 194°–195° C., $M^+$ 560.20.

Example 3: $X=6\text{-}CH_3O$; $X^1=7\text{-}CH_3O$; $X^2=H$; R, $R_4$, $R_5=H$; $Q^1$, $Q^2=H$; $A=-(CH_2)_2-$; $W=(-)$; $n=0$; $Y=3\text{-}CH_3O$; $Y^1=4\text{-}CH_3O$; and $Y^2=H$; m.p. 185°–186° C., $M^+$ 500.30.

Example 4: $X=6\text{-}C_2H_5O$; $X^1=7\text{-}C_2H_5O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=H$; m.p. 121°–122° C., $M^+$ 588.30.

Example 5: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; Y, $Y^1$ and $Y^2=H$; m.p. 219°–226° C., $M^+$ 500.20.

Example 6: $X=6\text{-}CH_3O$; $X^1=7\text{-}CH_3O$; $X^2=H$; R, $R_4$, $R_5=H$; Q, $Q^1$, $Q^2=H$; $A=-(CH_2)_2-$; $W=(-)$; $n=0$; Y, $Y^1$ and $Y^2=H$; m.p. 199°–201° C., $M^+$ 440.20.

Example 7: $X=6\text{-}CH_3O$; $X^1=7\text{-}CH_3O$; $X^2=H$; R, $R_4$, $R_5=H$; Q, $Q^1$, $Q^2=H$; $A=-(CH_2)_2-$; $W=(-)$; $n=0$; $Y=2\text{-}CH_3O$; $Y^1$ and $Y^2=H$; m.p. 140°–142° C., $M^+$ 471.00.

Example 8: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}CH_3O$; $Y^1$ and $Y^2=H$; m.p. 232.5°–234° C., $M^+$ 531.00.

Example 9: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-CH_2CH(CH_3)-$; $W=0$; $n=1$; Y, $Y^1$ and $Y^2=H$; m.p. 105°–107° C., $M^+$ 545.00.

Example 10: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=0$; $n=0$; $Y=2\text{-}I$; $Y^1=4\text{-}I$; and $Y^2=6\text{-}I$; m.p. 175°–180° C., $M^+$ 894.90.

Example 11: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}CH_3O$; $Y^1$ and $Y^2=H$; m.p. 113°–115.5° C., $M^+$ 531.00.

Example 12: $X=6\text{-}CH_3O$; $X^1=7\text{-}CH_3O$; $X^2=H$; R, $R_4$, $R_5=H$; Q, $Q^1$, $Q^2=H$; $A=-(CH_2)_2-$; $W=(-)$; $n=0$; $Y=4\text{-}CH_3O$; $Y^1$ and $Y^2=H$; m.p. 204°–205° C., $M^+$ 471.00.

Example 13: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}Cl$; $Y^1$ and $Y^2=H$; m.p. 130°–132.5° C., $M^{30}$ 535.00.

Example 14: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=5\text{-}CH_3O$; m.p. 217°–218° C., $M^+$ 591.10.

Example 15: X, $X^1$, $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=H$; m.p. 108°–109.5° C. (free base), $M^+$ 501.3.

Example 16: X, $X^1$, $X^2=H$; R, $R_4$, $R_5=H$; Q, $Q^1$, $Q^2=H$; $A=-(CH_2)_2-$; $W=(-)$; $n=0$; $Y=3\text{-}CH_3O$; $Y^1=4\text{-}CH_3O$; and $Y^2=H$; m.p. 123.5°–124.5° C. (free base), $M^+$ 441.20.

Example 17: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=S$; $n=1$; Y, $Y^1$ and $Y^2=H$; m.p. 112°–114° C., $M^+$ 533.2.

Example 18: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}NO_2$; $Y^1$ and $Y^2=H$; m.p. 210°–213° C., $M^+$ 546.3.

Example 19: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}CH_3O$; $Y^1=3\text{-}CH_3O$; and $Y^2=H$; m.p. 108°–111° C., $M^+$ 561.00.

Example 20: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $w=(-)$; $n=0$; $Y=3\text{-}CH_3O$; $Y^1=5\text{-}CH_3O$; and $Y^2=H$; m.p. 234°–235° C., $M^+$ 561.40.

Example 21: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}Cl$; and $Y^1$ and $Y^2=H$; m.p. 111°–113° C., $M^+$ 535.30.

Example 22: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}CH_3O$; $Y^1=5\text{-}CH_3O$; and $Y^2=H$; m.p. 201°–203° C., $M^+$ 561.40.

Example 23: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}CH_3$; and $Y^1$ and $Y^2=H$; m.p. 230°–323° C., $M^+$ 515.4.

Example 24: $X=6\text{-}CH_3O$; $X^1=7\text{-}CH_3O$; $X^2=8\text{-}CH_3O$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $X=3\text{-}CH_3O$; $Y^1=4\text{-}CH_3O$; and $Y^2=H$; m.p. 180°–182° C., $M^+$ 591.10.

Example 25: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}C_2H_5O$; $Y^1$ and $Y^2=H$; m.p. 105°–210° C., $M^+$ 545.00.

Example 26: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1$ and $Y^2=H$; m.p. 109°–111° C., $M^+$ 531.00.

Example 27: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}Br$; $Y^1=4\text{-}CH_3O$; and $Y^2=5\text{-}CH_3O$; m.p. 176°–179° C., $M^+$ 641.10.

Example 28: X, $X^1$, $X^2=H$; $Q=6\text{-}CH_3O$; $Q^1=7\text{-}CH_3O$; $Q^2=H$; R, $R_4$, $R_5=H$; $A=-(CH_2)_2-$; $W=(-)$; $n=0$; $Y=2\text{-}CH_3O$; $Y^1=3\text{-}CH_3O$; and $Y^2=H$; m.p. 208°–209° C., $M^+$ 501.10.

Example 29: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}Cl$; $Y^1=4\text{-}Cl$; and $Y^2=H$; m.p. 135°–138° C., $M^+$ 569.30.

Example 30: $X=6\text{-}CH_3O$; $X^1=7\text{-}CH_3O$; $X^2=H$; R, $R_4=H$; $R_5=3,4\text{-}(CH_3O)C_6H_3CH_2-$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=H$; m.p. 156°–159° C., $M^+$ 711.40.

Example 31: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=0$; $n=0$; $Y=2\text{-}Cl$; $Y^1$ and $Y^2=H$; m.p. 126.5°–128° C., $M^+$ 535.00.

Example 32: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=0$; $n=0$; $Y=4\text{-}Cl$; $Y^1$ and $Y^2=H$; m.p. 218°–219° C., $M^+$ 535.00.

Example 33: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=0$; $n=0$; $Y=4\text{-}Cl$; $Y^1$ and $Y^2=H$; m.p. 120°–122° C., $M^+$ 551.30.

Example 34: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y+Y^1=3,4-O-CH_2-O-$; and $Y^2=H$; m.p. 231.5°–233° C., $M^+$ 545.30.

Example 35: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=0$; $n=0$; $Y=4\text{-}CH_3O$; $Y^1$ and $Y^2=H$; m.p. 115°–119° C., $M^+$ 547.30.

Example 36: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-CH_2-$; $W=(-)$; $n=0$; $Y=2\text{-}CH_3O$; $Y^1=3-CH_3O$; and $Y^2=4-CH_3O$; m.p. 176.5°–178.5° C., $M^+$ 577.40.

Example 37: $X=6\text{-}CH_3O$; $X^1=7\text{-}CH_3O$; $X^2=H$; R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}OH$; $Y^1=3\text{-}C_2H_5O$; and $Y^2=H$; 138°–142° C., $M^+$ 561.30.

Example 38: $X=6\text{-}CH_3O$; $X^1=7\text{-}CH_3O$; $X^2=H$, R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=4\text{-}OH$; $Y^1=3\text{-}CH_3O$; and $Y^2=H$; m.p. 232°–235° C., $M^+$ 547.30.

Example 39: $X=6\text{-}CH_3O$; $X^1=7\text{-}CH_3O$; $X^2=H$, R, $R_4$, $R_5=H$; $Q^1$, $Q^2=H$; $A=-(CH_2)_2-$; $W=(-)$; $n=0$; $Y=3\text{-}CH_3O$; $Y^1$ and $Y^2=H$; m.p. 125.5°–141.4° C., $M^+$ 4671.20.

Example 40: $X=6\text{-}CH_3O$; $X^1=7\text{-}CH_3O$; $X^2=H$, R, $R_4$, $R_5=H$; $Q=6\text{-}CH_3O$; $Q^1=7\text{-}CH_3O$; $Q^2=H$; $A=-(CH_2)_2-$; $Y=3\text{-}C_6H_5CH_2O$; $Y^1=4\text{-}C_6H_5CH_2O$; and $Y^2=H$; m.p. 204°–206° C., $M^+$ 713.60.

Example 41: $X=6\text{-}CH_3O$; $X^1=7\text{-}CH_3O$; $X^2=H$, R, $R_4$, $R_5=H$; Q, $Q^1$, $Q^2=H$; $A=-(CH_2)_2-$; $W=(-)$; $n=0$; $Y=2\text{-}CH_3O$; $Y^1=3\text{-}CH_3O$; and $Y^2=H$; m.p. 189.5°–191.5° C., $M^+$ 501.30.

Example 42: $X=6\text{-}CH_3O$; $X^1=7\text{-}CH_3O$; $X^2=H$, R, $R_4$, $R_5=H$; $Q=7\text{-}CH_3O$; $Q^1=8\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=H$; m.p. 195°–196° C., $M^+$ 561.30.

Example 43: $X=6\text{-}CH_3O$; $X^1=7\text{-}CH_3O$; $X^2=H$, R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=3\text{-}CH_3O$; $Y^1=4\text{-}CH_3O$; and $Y^2=H$; m.p. 189°–191° C., $M^+$ 515.30.

Example 44: $X=6\text{-}CH_3O$; $X^1$, $X^2=H$, R, $R_4$, $R_5=H$; $Q=6\text{-}CH_3O$; $Q^1=7\text{-}CH_3O$; $Q^2=H$; $A=-(CH_2)_2-$; $W=(-)$; $n=0$; $Y=2\text{-}CH_3O$; $Y^1=3\text{-}CH_3O$; and $Y^2=H$; m.p. 212°–215° C., $M^+$ 531.00.

Example 45: $X=6\text{-}CH_3O$; $X^1$, $X^2=H$, R, $R_4$, $R_5=H$; $Q=6\text{-}CH_3O$; $Q^1=7\text{-}CH_3O$; $Q^2=H$; $A=-(CH_2)_2-$;

W=(—); n=0; Y=2-Cl; $Y^1$ and $Y^2$=H; m.p. 221°–223° C., M+ 505.20.

Example 46: X=6-$CH_3O$; $X^1$, $X^2$=H; R, $R_4$, $R_5$=H; Q=6-$CH_3O$; $Q^1$=7-$CH_3O$; $Q^2$=H; A=—$(CH_2)_2$—; W=(—); n=0; Y=3-$CH_3O$; $Y^1$=4-$CH_3O$; and $Y^2$=H; m.p. 206°–208° C., M+ 531.20.

Example 47: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=H; A=—($CH_3$)$CH_2CH_2$—; W=(—); n=0; Y, $Y^1$, $Y^2$=H; m.p. 198°–200° C., M+ 529.00.

Example 48: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=H; A=—$CH_2$—; W=(—); n=0; Y=4-$CH_3O$; $Y^1$ and $Y^2$=H; m.p. 155°–156° C.

Example 49: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=H; A=—$CH_2$—; W=(—); n=0; Y, $Y^1$, $Y^2$=H; m.p. 169°–171° C.; M+ 487.00.

Example 50: X=6-F; $X^1$=7-F; $X^2$=H; R, $R_4$, $R_5$=H; Q=6-$CH_3O$; $Q^1$=7-$CH_3O$; $Q^2$=H; A=—$(CH_2)_2$—; W=(—); n=0; Y=3-$CH_3O$; $Y^1$=4-$CH_3O$; and $Y^2$=H; m.p. 112°–114° C., M+ 537.3.

Example 51: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=H; A=—$(CH_2)_2$—; W=(—); n=0; Y=4-F; $Y^1$ and $Y^2$=H; m.p. 225°–227° C., M+ 519.30.

Example 52: X=6-$CH_3O$; $X^1$=7-$CH_3O$; $X^2$=H; R, $R_5$=H; $R_4$=$C_2H_5$; Q=6-$CH_3$; $Q^1$=7-$CH_3O$; $Q^2$=H; A=—$CH_2$—; W=(—); n=0; Y=4-$C_2H_5O$; $Y^1$ and $Y^2$=H; m.p. 201°–203° C., M+ 545.40.

Example 53: X=6-$CH_3O$; $X^1$=7-$CH_3O$; $X^2$=H; R, $R_5$=H; $R_4$=$C_2H_5$; Q, $Q^1$, $Q^2$=H; A=—$CH_2$—; W=(—); n=0; Y=4-$C_2H_5O$—; $Y^1$ and $Y^2$=H; m.p. 167°–168° C., M+ 485.30.

Example 54: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=H; A=—$(CH_2)_2$—; W=(—); n=0; Y=4-OH; $Y^1$ and $Y^2$=H; m.p. 151°–153° C., M+ 517.30.

Example 55: X=6-$CH_3O$; $X^1$=7-$CH_3O$; $X^2$=H; R, $R_4$, $R_5$=H; Q=6-$NO_2$; $Q^1$, $Q^2$=H; A=—$(CH_2)_2$—; W=(—); n=0; Y=3-$CH_3O$; $Y^1$=4-$CH_3O$; and $Y^2$=H; m.p. 212°–214° C., M+ 546.30.

Example 56: X, $X^1$=H; $X^2$=8-$CH_3O$; R, $R_4$, $R_5$=H; Q=6-$CH_3O$; $Q^1$=7-$CH_3O$; $Q^2$=H; A=—$(CH_2)_2$—; W=(—); n=0; Y=2-$CH_3O$; $Y^1$=3-$CH_3O$; and $Y^2$=H; m.p. 90°–92° C. (free base), M+ 531.30.

Example 57: X=6-$CH_3O$; $X^1$, $X^2$=H, R, $R_4$, $R_5$=H; Q=6-$CH_3O$; $Q^1$=7-$CH_3O$; $Q^2$=H; A=—$(CH_2)_2$—; W=(—); n=0; Y=2-Cl; $Y^1$ and $Y^2$=H; m.p. 212°–214° C., M+ 489.00.

Example 58: X=6-$CH_3O$; $X^1$=7-$CH_3O$; $X^2$=H; R, $R_4$, $R_5$=H; Q=6-$CH_3O$; $Q^1$, $Q^2$=H; A=—$(CH_2)_2$—; W=(—); n=0; Y=3-$CH_3O$; $Y^1$=4-$CH_3O$; and $Y^2$=H; m.p. 160°–162° C., M+ 531.00.

Example 59: X=6-$CH_3O$; $X^1$=7-$CH_3O$; $X^2$=H; R, $R_4$, $R_5$=H; Q=5-$CH_3O$; $Q^1$, $Q^2$=H; A=—$(CH_2)_2$—; W=(—); n=0; Y=3-$CH_3O$; $Y^1$=4-$CH_3O$; and $Y^2$=H; m.p. 197°–198.5° C., M+ 531.00.

Example 60: X=6-$CH_3O$; $X^1$=7-$CH_3O$; $X^2$=H; R, $R_4$, $R_5$=H; Q=6-$CH_3O$; $Q^1$=8-$CH_3O$, $Q^2$=H; A=—$(CH_2)_2$—; W=(—); n=0; Y=3-$CH_3O$; $Y^1$=4-$CH_3O$; and $Y^2$=H; m.p. 146°–149° C, M+ 561.30.

Example 61: X=6-$CH_3O$; $X^1$=7-$CH_3O$; $X^2$=H; R, $R_4$, $R_5$=H; Q=7-Cl; $Q^1$, $Q^2$=H; A=—$(CH_2)_2$—; W=(—); n=0; Y=3-$CH_3O$; $Y^1$=4-$CH_3O$; and $Y^2$=H; m.p. 190°–193° C., M+ 535.00.

Example 62: X=6-$CH_3O$; $X^1$=7-$CH_3O$; $X^2$=H; R, $R_4$, $R_5$=H; Q=5-$CH_3O$; $Q^1$, $Q^2$=H; A=—$(CH_2)_2$—; W=(—); n=0; Y=2-$CH_3O$; $Y^1$=3-$CH_3O$; and $Y^2$=H; m.p. 199°–200° C., M+ 531.00.

Example 63: X=6-$CH_3O$; $X^1$=7-$CH_3O$; $X^2$=H; R, $R_4$, $R_5$=H; Q=5-$CH_3O$; $Q^1$, $Q^2$=H; A=—$(CH_2)_2$—; W=(—); n=0; Y=2-Cl; $Y^1$ and $Y^2$=H; m.p. 210°–211° C., M+ 505.30.

Example 64: X=6-$CH_3O$; $X^1$=7-$CH_3O$; $X^2$=H; R=$C_2H_5O$; $R_4$, $R_5$=H; Q=6-$CH_3O$; $Q^1$=7-$CH_3O$; $Q^2$=8-$CH_3O$; A=—$(CH_2)_2$—; W=(—); n=0; Y=3-$CH_3O$; $Y^1$=4-$CH_3O$; and $Y^2$=H; m.p. 138°–140° C., M+ 635.00.

Example 65: X=6-$CH_3O$; $X^1$=7-$CH_3O$; $X^2$=H; R=$CH_3O$; $R_4$, $R_5$=H; Q=7-$CH_3O$; $Q^1$=8-$CH_3O$; $Q^2$=H; A=—$(CH_2)_2$—; W=(—); n=0; Y=3-$CH_3O$; $Y^1$=4-$CH_3O$; and $Y^2$=H; m.p. 178°–180° C., M+ 591.50.

Example 66: X=6-$CH_3O$; $X^1$=7-$CH_3O$; $X^2$=H; R=$C_2H_5O$—; $R_4$, $R_5$=H; Q=6-$CH_3O$; $Q^1$, $Q^2$=H; A=—$(CH_2)_2$—; W=(—); n=0; Y=3-$CH_3O$; $Y^1$=4-$CH_3O$; and $Y^2$=H; m.p. 86°–88° C., M+ 575.40.

Example 67: X=6-$CH_3O$; $X^1$=7-$CH_3O$; $X^2$=H; R=$C_2H_5O$—; $R_4$, $R_5$=H; Q=7-$CH_3O$; $Q^1$=8-$CH_3O$; $Q^2$=H; A=—$(CH_2)_2$—; W=(—); n=0; Y=3-$CH_3O$; $Y^1$=4-$CH_3O$; and $Y^2$=H; m.p. 168°–169° C., M+ 605.40.

Example 68: X=H; $X^1$=7-$CH_3O$; $X^2$=8-$CH_3O$; R, $R_4$, $R_5$=H; Q=6-$CH_3O$; $Q^1$=7-$CH_3O$; $Q^2$=H; A=—$(CH_2)_2$—; W=(—); n=0; Y=3-$CH_3O$; $Y^1$=4-$CH_3O$; and $Y^2$=H; m.p. 138°–140° C., M+ 561.40.

Example 69: X=6-$CH_3O$; $X^1$=7-$CH_3O$; $X^2$=H; R, $R_4$, $R_5$=H; Q=6-$CH_3O$; $Q^1$=7-$CH_3O$; $Q^2$=8-$CH_3O$; A=—$(CH_2)_2$—; W=(—); n=0; Y=3-$CH_3O$; $Y^1$=4l-$CH_3O$; and $Y^2$=H; m.p. 157°–158° C., M+ 591.30.

Example 70: X=H; $X^1$=7-$CH_3O$; $X^2$=8-$CH_3O$; R, $R_4$, $R_5$=H; Q=6-$CH_3O$; $Q^1$=7-$CH_3O$; $Q^2$=H; A=—$(CH_2)_2$—; W=(—); n=0; Y=3-$CH_3O$; $Y^1$=4-$CH_3O$; and $Y^2$=H; m.p. 147.5°–151° C., M+ 561.40.

Example 71: X=6-$CH_3O$; $X^1$=7-$CH_3O$; $X^2$=H; R, $R_4$, $R_5$=H; Q, $Q^1$, $Q^2$=H; A=—$(CH_2)_2$—; W=(—); n=0; Y=3-$CH_3O$; $Y^1$=4-OH; and $Y^2$=H; m.p. 169°–171.5° C., M+ 487.20.

EXAMPLES 72–106

Using the procedure of Example 1, and starting with the requisite reagents, the following compounds were prepared as their hydrochloride salts unless indicated otherwise:

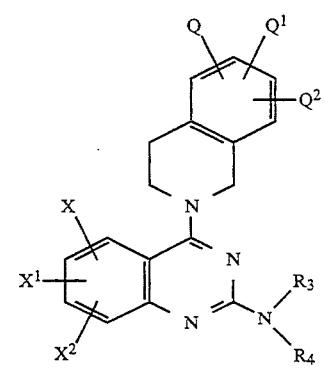

Example 72: X=6-$CH_3O$; $X^1$=7-$CH_3O$; $X^2$=H; Q, $Q^1$, $Q^2$=H;

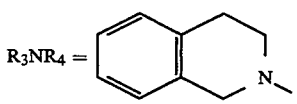

m.p. 181°–182° C.; M+ 452.20.

Example 73: X=6-CH$_3$O; X$^1$=7-CH$_3$O; X$^2$=H; Q, Q$^1$, Q$^2$=H;

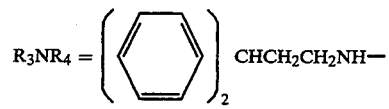

m.p. 224°–225° C.; M+ 531.20.

Example 74: X=6-CH$_3$O; X$^1$=7-CH$_3$O; X$^2$=H; Q=6-CH$_3$O; Q$^1$=7-CH$_3$O; Q$^2$=H;

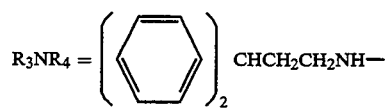

m.p. 226°–229° C.; M+ 531.20.

Example 75: X=6-CH$_3$O; X$^1$=7-CH$_3$O; X$^2$=H; Q=6-CH$_3$O; Q$^1$=7-CH$_3$O; Q$^2$=H;

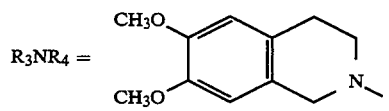

m.p. 181°–183° C.; M+ 572.30.

Example 76: X=6-CH$_3$O; X$^1$=7-CH$_3$O; X$^2$=H; Q, Q$^1$, Q$^2$=H;

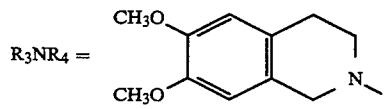

m.p. 154°–156° C.; M+ 512.10.

Example 77: X=6-CH$_3$O; X$^1$=7-CH$_3$O; X$^2$=H; Q=6-CH$_3$O; Q$^1$=7-CH$_3$O; Q$^2$=H;

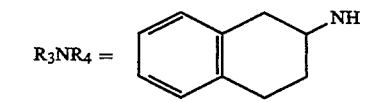

m.p. 145.5°–148° C.; M+ 527.00.

Example 78: X=6-CH$_3$O; X$^1$=7-CH$_3$CH$_2$CH$_2$O; X$^2$=H; Q=6-CH$_3$O; Q$^1$=7-CH$_3$O; Q$^2$=H;

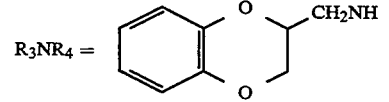

m.p. 170°–171° C.; M+ 573.20.

Example 79: X=6-C$_2$H$_5$O; X$^1$=7-C$_2$H$_5$O; X$^2$=H; Q=6-CH$_3$O; Q$^1$=7-CH$_3$O; Q$^2$=H;

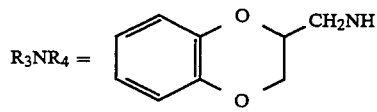

m.p. 196°–200° C.; M+ 573.20.

Example 80: X=6-CH$_3$O; X$^1$=7-CH$_3$O; X$^2$=H; Q=6-CH$_3$O; Q$^1$=7-CH$_3$O; Q$^2$=H;

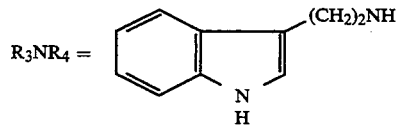

m.p. 233°–235° C.; M+ 540.00.

Example 81: X=6-CH$_3$O; X$^1$=7-CH$_3$O; X$^2$=H; Q=6-CH$_3$O; Q$^1$=7-CH$_3$O; Q$^2$=H;

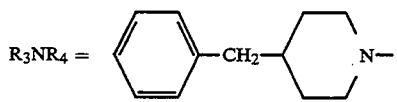

m.p. 133°–135.5° C.; M+ 555.00.

Example 82: X=6-CH$_3$O; X$^1$=7-CH$_3$O; X$^2$=H; Q=6-CH$_3$O; Q$^1$=7-CH$_3$O; Q$^2$=H;

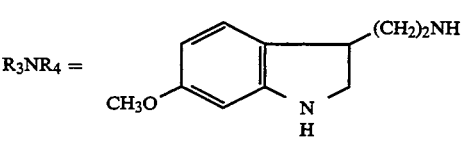

m.p. 225°–227° C.; M+ 570.20.

Example 83: X=6-CH$_3$O; X$^1$=7-CH$_3$O; X$^2$=H; Q=6-CH$_3$O; Q$^1$=7-CH$_3$O; Q$^2$=H;

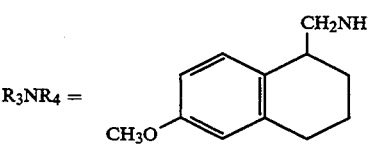

m.p. 200°–221° C. (dec); M+ 571.00.

Example 84: X=6-CH$_3$O; X$^1$=7-CH$_3$O; X$^2$=H; Q=6-CH$_3$O; Q$^1$=7-CH$_3$O; Q$^2$=H;

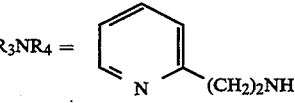

m.p. 186.5°–188° C. (free base); M+ 502.20.

Example 85: X=6-CH$_3$O; X$^1$=7-CH$_3$O; X$^2$=H; Q=6-CH$_3$O; Q$^1$=7-CH$_3$O; Q$^2$=H;

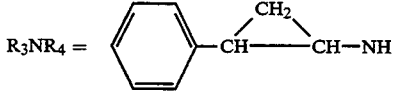

m.p. 202.5°–204.5° C.; M+ 513.20.

Example 86: X, $X^1$, $X^2$=H; Q=6-$CH_3O$; $Q^1$=7-$CH_3O$; $Q^2$=H;

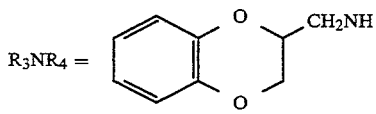

m.p. 158°–159° C. (free base); M+ 484.53.

Example 87: X=6-$CH_3O$; $X^1$=7-$CH_3O$; $X^2$=8-$CH_3O$; Q=6-$CH_3O$; $Q^1$=7-$CH_3O$; $Q^2$=H;

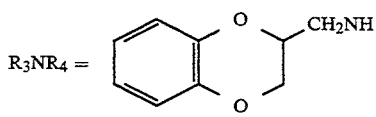

m.p. 214°–217° C.; M+ 574.3.

Example 88: X, $X^1$, $X^2$=H; Q=6-$CH_3O$; $Q^1$=7-$CH_3O$; $Q^2$=H;

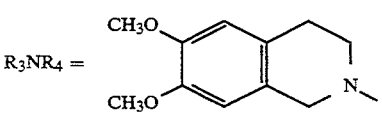

m.p. 148°–150° C. (free base); M+ 512.2.

Example 89: X=6-$CH_3O$; $X^1$=7-$CH_3O$; $X^2$=H; Q=6-$CH_3O$; $Q^1$=7-$CH_3O$; $Q^2$=H;

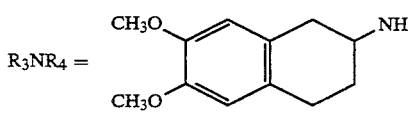

m.p. 163°–167° C.; M+ 587.30.

Example 90: X=6-$CH_3O$; $X^1$=7-$CH_3O$; $X^2$=H; Q=6-$CH_3O$; $Q^1$=7-$CH_3O$; $Q^2$=H;

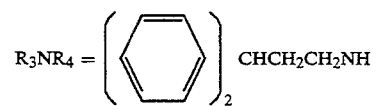

m.p. 134°–136.5° C.; M+ 577.40.

Example 91: X=6-$CH_3O$; $X^1$=7-$CH_3O$; $X^2$=H; Q=6-$CH_3O$; $Q^1$=7-$CH_3O$; $Q^2$=H;

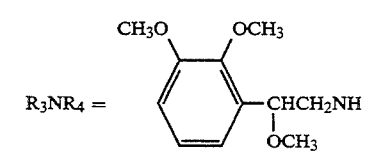

m.p. 211°–213° C.; M+ 591.20.

Example 92: X=6-$CH_3O$; $X^1$=7-$CH_3O$; $X^2$=H; Q=6-$CH_3O$; $Q^1$=7-$CH_3O$; $Q^2$=H;

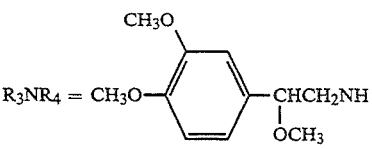

m.p. 214°–216° C.; M+ 591.30.

Example 93: X=6-$CH_3$; $X^1$, $X^2$=H; Q=6-$CH_3O$; $Q^1$=7-$CH_3O$; $Q^2$=H;

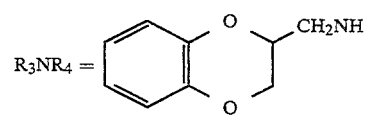

m.p. 192°–194° C.; M+ 499.20.

Example 94: X=6-$CH_3O$; $X^1$=7-$CH_3O$; $X^2$=H; Q, $Q^1$, $Q^2$=H;

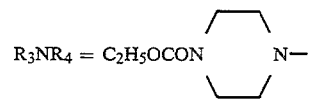

m.p. 155°–156° C.; M+ 478.00.

Example 95: X=6-$CH_3O$; $X^1$=7-$CH_3O$; $X^2$=H; Q, $Q^1$, $Q^2$=H;

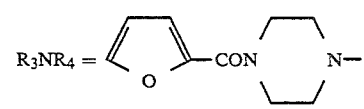

m.p. 225°–235° C.; M+ 500.00.

Example 96: X=6-$CH_3O$; $X^1$=7-$CH_3O$; $X^2$=H; Q=6-$CH_3O$; $Q^1$=7-$CH_3O$; $Q^2$=H;

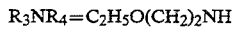

m.p. 185°–186° C.; M+.

Example 97: X=6-$CH_3O$; $X^1$=7-$CH_3O$; $X^2$=H; Q=6-$CH_3O$; $Q^1$=7-$CH_3O$; $Q^2$=H;

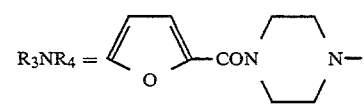

m.p. 240°–242° C.; M+ 560.00.

Example 98: X=6-$CH_3O$; $X^1$=7-$CH_3O$; $X^2$=H; Q=6-$CH_3O$; $Q^1$=7-$CH_3O$; $Q^2$=H;

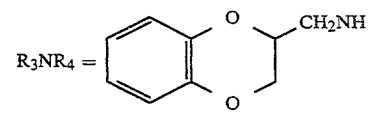

m.p. 238.5°–240° C.; M+ 545.00.

Example 99: X=6-$CH_3O$; $X^1$=7-$CH_3O$; $X^2$=H; Q=6-$CH_3O$; $Q^1$=7-$CH_3O$; $Q^2$=H;

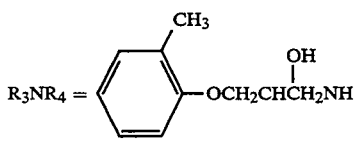

m.p. 232°–233° C.; M+ 561.00.

Example 100: X=6-CH$_3$O; X$^1$=7-CH$_3$O; X$^2$=H; Q=6-CH$_3$O; Q$^1$=7-CH$_3$O; Q$^2$=H;

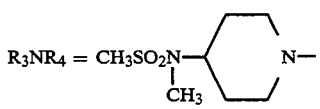

m.p. 229°–230° C.; M+ 572.00.

Example 101: X=6-CH$_3$O; X$^1$=7-CH$_3$O; X$^2$=H; Q=6-CH$_3$O; Q$^1$=7-CH$_3$O; Q$^2$=H;

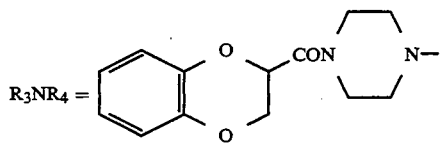

m.p. 165°–168 dec° C.; M+ 628.00.

Example 102: X=6-CH$_3$O; X$^1$=7-CH$_3$O; X$^2$=H; Q, Q$^1$, Q$^2$=H;

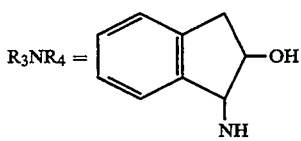

m.p. 206°–210° C.; M+ 469.30.

Example 103: X=6-CH$_3$O; X$^1$=7-CH$_3$O; X$^2$=H; Q=H; Q$^1$=7-CH$_3$O; Q$^2$=8-CH$_3$O;

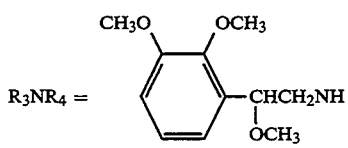

m.p. 200°–202° C.; M+ 591.00.

Example 104: X=6-CH$_3$O; X$^1$=7-CH$_3$O; X$^2$=H; Q=6-CH$_3$O; Q$^1$=7-CH$_3$O; Q$^2$=H;

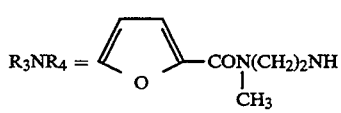

M+ 548.30.

Example 105: X=6-CH$_3$O; X$^1$=7-CH$_3$O; X$^2$=H; Q=6-CH$_3$O; Q$^1$=7-CH$_3$O; Q$^2$=H;

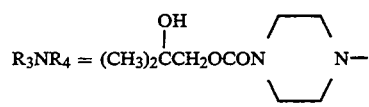

m.p. 168°–170° C.; M+ 582.30.

Example 106: X=6-CH$_3$O; X$^1$=7-CH$_3$O; X$^2$=H; Q=6-CH$_3$O; Q$^1$=7-CH$_3$O; Q$^2$=H;

R$_3$NR$_4$=(CH$_3$OCH$_2$CH$_2$)$_2$)N— m.p. °C.; M+ 513.00.

EXAMPLE 107

2-(3,4-Dimethoxyphenethylamino)-4-(2,3,4,5-tetrahydro-2-benzoazep-2-yl)-6,7-dimethoxyquinazoline hydrochloride (I: X=6-CH$_3$O; X$^1$=7-CH$_3$O; R$_1$R$_2$N=2,3,4,5-tetrahydro-2-benzazep-2-yl; R$_3$=3,4-(CH$_3$O)$_2$C$_6$H$_3$(CH$_2$)$_2$—; and R$_4$=H)

A.
2-chloro-4-(2,3,4,5-tetrahydrobenzazep-2-yl)-6,7-dimethoxyquinazoline

A mixture of 1.0 g of 2,3,4,5-tetrahydro-2-benzazepine, 1.76 g of 2,4-dichloro-6,7-dimethoxyqinazoline and 1.0 g of triethylamine in 25 ml of methylene chloride was stirred at room temperature under nitrogen for three hours. An additional 290 mg of the benzazepine was added and stirring continued over 48 hours. The reaction mixture was diluted with 100 ml of methylene chloride and the organic solution washed successively with 1N hydrochloric acid (3×75 ml), water (2×75 ml), a saturated sodium bicarbonate solution (2×75 ml), water (2×75 ml) and a brine solution (1×75 ml). The organic phase was separated, dried over sodium sulfate and concentrated to a foam, 2.15 g. The residue was treated with reluxing methanol and cooled in a refrigerator. The resulting solids were filtered and dried, 1.84 g. A small sample was recrystallized from methanol, m.p. 164°–165° C.

B.
2-(3,4-dimethoxyphenethylamino)-4-(2,3,4,5-tetrahydrobenzazep-2-yl)-6,7-dimethoxyquinazoline hydrochloride A mixture of 1.109 g of the product of Example 107A, 543 mg of 3,4-dimethoxyphenethylamine and 387 mg of diisopropylethylamine in 1.1 g ethoxyethoxyethanol was stirred under nitrogen at 170° C. for five hours. The reaction mixture was cooled to room temperature and diluted with 5 ml of methylene chloride. This solution was chromatographed without pressure on 60 g of silica gel using methylene chloride as the eluent, taking 15 fractions. Fractions 3–6 were combined and the elution continued under pressure with 2% methanol-methylene chloride, taking 14 fractions. Fractions 8–12 were combined and concentrated to give an oil which was dissolved in 6 ml of 1N hydrogen chloride in methanol. The resulting solids were filtered and dried, 679 mg, m.p. 226°–228° C. Fractions 3–6 when carried through the same procedure gave 170 mg of the hydrochloride salt.

Anal. Calc'd for C$_{30}$H$_{34}$N$_4$O$_4$.HCl: C, 65.4, H, 10.2; N, 6.4. Found: C, 65.3; H, 10.1; N, 6.5.

EXAMPLES 108–138

Employing the procedure of Example 107 and starting with the appropriate reagents, the following compounds were prepared:

Example 108: $X=6\text{-}CH_3O$; $X^1=7\text{-}CH_3O$; $X^2=H$; R, $R_5=H$; $Q=6\text{-}CH_3O$; $Q^1=7\text{-}CH_3O$; $Q^2=H$, $m=0$; $p=1$;

$$R_3R_4N = \text{(2,3-methylenedioxybenzyl)amine with extra O-CH}_2\text{-NH group}$$

m.p. 205°–206° C.; M+ 531.2.

Example 109: $X=6\text{-}CH_3O$; $X^1=7\text{-}CH_3O$ $X^2=H$; R, $R_5=H$; Q, $Q^1=H$; $Q^2=8\text{-}CH_3O$; $m=0$; $p=1$; $R_3R_4N=3,4\text{-}(CH_3O)_2C_6H_3(CH_2)_2NH$; m.p. 187°–188° C.; M+ 531.0.

Example 110: $X=6\text{-}CH_3$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2\text{-}ClC_6H_4(CH_2)_2NH$; m.p. 156°–157° C.; M+ 489.0.

Example 111: $X=6\text{-}CH_3O$; $X^1=7\text{-}CH_3O$; $X^2=H$; R, $R_5=H$; $Q=5\text{-}CH_3O$; $Q^1=6\text{-}CH_3O$; $Q^2=H$; $m=0$; $p=1$; $R_3R_4N=3,4\text{-}(CH_3O)_2C_6H_3(CH_2)_2NH$; m.p. 175°–177° C.; M+ 561.1.

Example 112: $X=6\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2\text{-}ClC_6H_4(CH_2)_2NH$; m.p. 241°–242° C.; M+ 509.03.

Example 113: $X=5\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2\text{-}ClC_6H_4(CH_2)_2NH$; m.p. 166°–167° C.; M+ 509.0.

Example 114: $X=6\text{-}CH_3O$; $X^1=7\text{-}CH_3O$; $X^2=H$; $Q=5\text{-}CH_3O$; $Q^1=6\text{-}CH_3O$; $Q^2=H$; R, $R_5=H$; $m=0$; $p=1$; $R_3R_4N=2,3\text{-}(CH_3O)_2C_6H_3(CH_2)_2NH$; m.p. 209° C.; M+ 561.27.

Example 115: $X=5\text{-}Cl$; $X^1$, $X^2=H$; R, $R_5=H$; $Q=6\text{-}CH_2O$; $Q^1=7\text{-}CH_3O$; $Q^2=H$; $m=0$; $p=1$; $R_3R_4N=3,4\text{-}(CH_3O)_2C_6H_3(CH_2)_2NH$; m.p. 106°–107° C.; M+ 535.3.

Example 116: $X=5\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2,3\text{-}(CH_3O)_2C_6H_3(CH_2)_2NH$; m.p. 200°–202° C.; M+ 535.20.

Example 117: $X=6\text{-}CH_3O$; $X^1=7\text{-}CH_3O$; $X^2=H$; R, $R_5=H$; $Q=H$; $Q^1=7\text{-}CH_3O$; $Q^2=8\text{-}CH_3O$; $m=0$; $p=1$; $R_3R_4N=2,3\text{-}(CH_3O)_2C_6H_3(CH_2)_2NH$; m.p. 194.5°–195.5° C.; M+ 561.0.

Example 118: $X=5\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=3,4\text{-}(CH_3O)_2C_6H_3(CH_2)_2NH$; m.p. 197°–198° C.; M+ 531.4.

Example 119: $X=6\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2,3\text{-}(CH_3O)_2C_6H_3(CH_2)_2NH$; m.p. 214°–215° C.; M+ 535.40.

Example 120: $X=5\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2,3\text{-}(CH_3O)_2C_6H_3(CH_2)_2NH$; m.p. 178°–179° C.; M+ 531.4.

Example 121: $X=5\text{-}Cl$; $X^1$, $X^2=H$; R, $R_5=H$; $Q=6\text{-}CH_3O$; $Q^1=7\text{-}CH_3O$; $Q^2=H$; $m=0$; $p=1$; $R_3R_4N=2\text{-}ClC_6H_4(CH_2)_2NH$; m.p. 178°–179° C.; M+ 505.3.

Example 122: $X=6\text{-}CH_3O$; $X^1=7\text{-}CH_3O$; $X^2=H$; R, $R_5=H$; $Q=6\text{-}CH_3O$; $Q^1=7\text{-}CH_3O$; $Q^2=H$; $m=0$; $p=1$; $R_3R_4N=2\text{-}I\text{-}4,5\text{-}(CH_3O)_2C_6H_2(CH_2)_2NH$; m.p. 216°–217° C. (free base); M+ 687.0.

Example 123: $X=6\text{-}CH_3O$; $X^1=7\text{-}CH_3O$; $X^2=H$; R, $R_5=H$; $Q=H$; $Q^1=7\text{-}CH_2O$; $Q^2=8\text{-}CH_2O$; $m=0$; $p=1$; $R_3R_4N=2\text{-}ClC_6H_4(CH_2)_2NH$; m.p. 197°–198° C.; M+ 547.1.

Example 124: $X=6\text{-}CH_3O$; $X^1=7\text{-}CH_3O$; $X^2=H$; $R=CH_3O$; $R_5=H$; $Q=6\text{-}F$; $Q^1$, $Q^2=H$; $m=0$; $p=1$; $R_3R_4N=3,4\text{-}(CH_3O)_2C_6H_3(CH_2)_2NH$; m.p. 215°–217° C.; M+ 548.6.

Example 125: $X=6\text{-}CH_3O$; $X^1=7\text{-}CH_3O$; $X^2=H$; R, $R_5=H$; Q, $Q^1=H$; $Q^2=7\text{-}CH_3$; $m=0$; $p=1$; $R_3R_4N=3,4\text{-}(CH_3O)_2C_6H_3(CH_2)_2NH$; m.p. 182°–183° C.; M+ 515.3.

Example 126: $X=6\text{-}CH_3O$; $X^1=7\text{-}CH_3O$; $X^2=H$; R, $R_5=H$; Q, $Q^1$, $Q^2=H$; $m=1$; $p=1$; $R_3R_4N=2,3\text{-}(CH_3O)_2C_6H_3(CH_2)_2NH$; m.p. 222°–223° C.; M+ 515.3.

Example 127: $X=6\text{-}CH_3O$; $X^1=7\text{-}CH_3O$; $X^2=H$; $R_5=H$; Q, $Q^1$, $Q^2=H$; $m=1$; $p=1$; $R_3R_4N=2\text{-}ClC_6H_4(CH_2)_2NH$; m.p. 218°–219° C.; M+ 489.2.

Example 128: $X=6\text{-}CH_3O$; $X^1=7\text{-}CH_3O$; $X^2=H$; R, $R_5=H$; $Q=6\text{-}CH_3O$; $Q^1=7\text{-}CH_3O$; $Q^2=H$; $m=0$; $p=1$; $R_3R_4N=3,4,5\text{-}(CH_3O)_3C_6H_2(CH_2)_2NH$; m.p. 142°–150° C.; M+ 591.4.

Example 129: $X=6\text{-}CH_3O$; $X^1=7\text{-}CH_3O$; $X^2=H$; $R=H$; $R_5=3,4\text{-}(CH_3O)_2C_6H_3CH_2$; $Q=6\text{-}CH_3O$; $Q^1=7\text{-}CH_3O$; $Q^2=H$; $m=0$; $p=1$; $R_3R_4N=2\text{-}ClC_6H_4(CH_2)_2NH$; m.p. 234°–235° C.; M+ 671.2.

Example 130: $X=6\text{-}CH_3O$; $X^1=7\text{-}CH_3O$; $X^2=H$; $R=H$; $R_5=3,4\text{-}(CH_3O)_2C_6H_3CH_2$; $Q=6\text{-}CH_3O$; $Q^1=7\text{-}CH_3O$; $Q^2=H$; $m=0$; $p=1$; $R_3R_4N=2,3\text{-}(CH_3O)_2C_6H_3(CH_2)_2NH$; m.p. 144°–145° C.; M+ 697.3.

Example 131: $X=6\text{-}CH_3O$; $X^1=7\text{-}CH_3O$; $X^2=H$; $R=CH_3O$; $R_5=H$; Q, $Q^1$, $Q^2=H$; $m=0$; $p=1$; $R_3R_4N=2,3\text{-}(CH_3O)_2C_6H_3(CH_2)_2NH$; m.p. 120°–123° C.; M+ 531.2.

Example 132: $X=6\text{-}CH_3O$; $X^1=7\text{-}CH_3O$; $X^2=H$; $R=CH_3O$; $R_5=H$; Q, $Q^1$, $Q^2=H$; $m=0$; $p=1$; $R_3R_4N=3,4\text{-}(CH_3O)_2C_6H_3(CH_2)_2NH$; m.p. 206°–208° C.; M+ 531.6.

Example 133: $X=6\text{-}CH_3O$; $X^1=7\text{-}CH_3O$; $X^2=H$; R, $R_5=H$; Q, $Q^1$, $Q^2=H$; $m=1$; $p=1$; $R_3R_4N=3,4\text{-}(CH_3O)_2C_6H_3(CH_2)_2NH$; m.p. 217°–219° C.; M+ 515.5.

Example 134: $X=6\text{-}CH_3O$; $X^1=7\text{-}CH_3O$; $X^2=H$; R, $R_5=H$; Q, $Q^2=H$; $Q^1=7\text{-}NH_2$; $m=1$; $p=1$; $R_3R_4N=3,4\text{-}(CH_3O)_2C_6H_3(CH_2)_2NH$; m.p. 213°–217° C. (free base); M+ 530.2.

Example 135: $X=6\text{-}CH_3O$; $X^1=7\text{-}CH_3O$; $X^2=H$; $R=H$; $R_5=3,4\text{-}(CH_3O)_2C_6H_3CH_2$; $Q=6\text{-}CH_3O$; $Q^1=7\text{-}CH_3O$; $Q^2=H$; $m=0$; $p=1$; $R_3R_4N=3,4\text{-}(CH_3O)_2C_6H_3(CH_2)_2NH$; m.p. 208°–209° C.; M+ 711.4.

Example 136: $X=6\text{-}CH_3O$; $X^1=7\text{-}CH_3O$; $X^2=H$; $R=CH_3O$; $R_5=H$; $Q=H$; $Q^1=7\text{-}CH_3O$; $Q^2=8\text{-}CH_3O$;

m=0; p=1; $R_3R_4N=3,4-(CH_3O)_2C_6H_3CH(CH_3O)(CH_2)_2NH$; m.p. 159°-161° C. (free base); M+ 621.4.

Example 137: $X=6-CH_3O$; $X^1=7-CH_3O$; $X^2=H$; R, $R_5=H$; Q=5-OH; $Q^1=6-CH_3O$; $Q^2=H$; m=0; p=1; $R_3R_4N=2,3-(CH_3O)_2C_6H_3(CH_2)_2NH$; m.p. 190°-200° C.; M+ 547.0.

Example 138: $X=6-CH_3O$; $X^1=7-CH_3O$; $X^2=H$; R, $R_5=H$; $Q=6-CH_3O$; $Q^1=7-CH_3O$; $Q^2=H$; m=0; p=1; $R_3R_4N=2-Br-4,5-(CH_3O)_2C_6H_2(CH_2)_2NH$; m.p. 176°-179° C.; M+ 641.0.

Example 139: $X=5-CH_3$; $X^1$, $X^2=H$; R, $R_5=H$; $Q=6-CH_3O$; $Q^1=7-CH_3O$; $Q^2=H$; m=0; p=1; $R_3R_4N=3,4-(CH_3O)_2C_6H_3(CH_2)_2NH$; m.p. 141°-142° C.; M+ 515.0.

EXAMPLES 140-147

Using the procedure of Example 107 and starting with the necessary reagents, the following compounds were prepared:

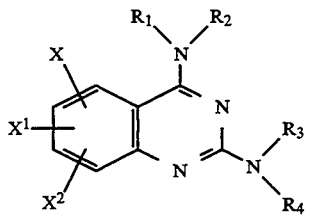

Example 140: $X-CH_3O$; $X^1=7-CH_3O$; $X^2=H$

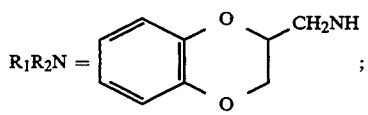

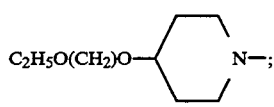

m.p. 204°-207° C.; M+ 545.2.

Example 141: $X=6-CH_3O$; $X^1=7-CH_3O$; $X^2=H$; $R_1R_2N=$

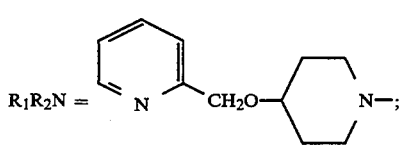

$R_3R_4=2,4-(CH_3O)_2C_6H_3CH_2NH$; m.p. 117°-119° (free base); M+ 527.0.

Example 142: $X=6-CH_3O$; $X^1=7-CH_3O$; $X^2=H$;

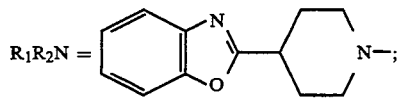

$R_3R_4N=2,4-(CH_3O)_2C_6H_3CH_2NH$; m.p. 146°-147° C. (free base); M+ 621.4.

Example 143: X, $X^1$, $X^2=H$; $R_1R_2N=C_6H_{11}NH-$; $R_3R_4N=C_6H_{11}NH$; m.p. 162°-165° C. (free base); M+ 325.0.

Example 144: $X=6-CH_3O$; $X^1=7-CH_3O$; $X^2=H$;

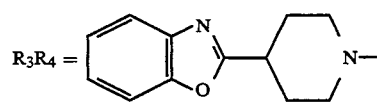

m.p. 215°-217° C. (free base); M+ 591.0.

Example 145: $X=6-CH_3O$; $X^1=7-CH_3O$; $X^2=H$;

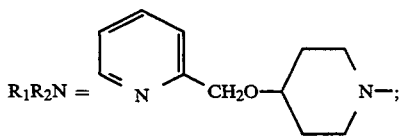

m.p. 220° C.; M+ 507.0.

Example 146: $X=6-N(CH_3)_2$; $X^1$ $X^2=H$;

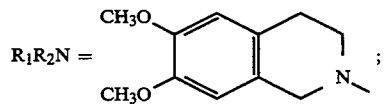

$R_3R_3N=3,4-(CH_3O)_2C_6H_3(CH_2)_2NH$; m.p. 193.5°-194.5° C.; M+ 544.3.

Example 147: $X=6-CH_3O$; $X^1=7-CH_3O$; $X^2=H$;

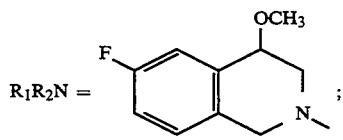

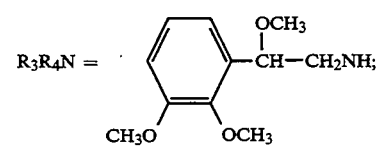

m.p. 156°-158° C.; M+ 579.3.

PREPARATION A

Employing the procedure of Example 1A and starting with appropriate reagents, the following intermediates were prepared:

[Structure diagram showing a tetrahydroisoquinoline with substituents Q, Q¹, Q², R on one ring system connected via N to a phenyl ring bearing X, X¹, X², R₅ substituents and an N=C(Cl)–N group]

Compound 1: $X=6\text{-}CH_3O$; $X^1=7\text{-}C_3H_7O$; $X^2=H$; $Q=6\text{-}CH_3O$; $Q^1=7\text{-}CH_3O$; $Q^2=H$; R, $R_5=H$; m.p. 120°–121° C.

Compound 2: $X=6\text{-}C_2H_5O$; $X^1=7\text{-}C_2H_5O$; $X^2=H$; $Q=6\text{-}CH_3O$; $Q^1=7\text{-}CH_3O$; $Q^2=H$; R, $R_5=H$; m.p. 161°–162° C.

Compound 3: $X=6\text{-}CH_3O$; $X^1=7\text{-}C_3O$; $X^2=H$; Q, $Q^1$, $Q^2=H$; R, $R_5=H$; m.p. 169°–171° C.

Compound 4: $X=6\text{-}CH_3O$; $X^1=7\text{-}C_3O$; $X^2=H$; $Q=6\text{-}CH_3O$; $Q^1=7\text{-}CH_3O$; $Q^2=H$; R, $R_5=H$; m.p. 183°–186° C.

Compound 5: X, $X^1$, $X^2=H$; $Q=6\text{-}CH_3O$; $Q^1=7\text{-}CH_3O$; $Q^2=H$; R, $R_5=H$; m.p. 126°–126.5° C.

Compound 6: $X=6\text{-}CH_3O$; $X^1=7\text{-}C_3O$; $X^2=8\text{-}CH_3O$; $Q=6\text{-}CH_3O$; $Q^1=7\text{-}CH_3O$; $Q^2=H$; R, $R_5=H$; m.p. 130°–131° C.

Compound 7: $X=6\text{-}CH_3O$; $X^1=7\text{-}C_3O$; $X^2=H$; $Q=6\text{-}CH_3O$; $Q^1=7\text{-}CH_3O$; $Q^2=H$; $R_5=3,4\text{-}(CH_3O)_2C_6H_3CH_2$; $R=H$; m.p. 154°–156.5° C.

Compound 8: $X=6\text{-}CH_3O$; $X^1=7\text{-}C_3O$; $X^2=H$; $Q=H$; $Q^1=7\text{-}CH_3O$; $Q^2=8\text{-}CH_3O$; R, $R_5=H$; m.p. 162°–163° C.

Compound 9: $X=6\text{-}CH_3O$; $X^1$, $X^2=H$; $Q=6\text{-}CH_3O$; $Q^1=7\text{-}CH_3O$; $Q^2=H$; R, $R_5=H$; m.p. 132°–134° C.

Compound 10: $X=6\text{-}CH_3$; $X^1$, $X^2=H$; $Q=6\text{-}CH_3O$; $Q^1=7\text{-}CH_3O$; $Q^2=H$; R, $R_5=H$; m.p. 133°–135° C.

Compound 11: X, $X^1$, $X^2=H$, Q, $Q^1$, $Q^2=H$; R, $R_5=H$; m.p. 130°–131° C.

Compound 12: $X=6\text{-}F$; $X^1=7\text{-}F$; $X^2=H$; $Q=6\text{-}CH_3O$; $Q^1=7\text{-}CH_3O$; $Q^2=H$; R, $R_5=H$; m.p. 219°–220° C.

Compound 13: $X=6\text{-}CH_3O$; $X^1=7\text{-}CH_3O$; $X^2=H$; Q, $Q^2=H$; $Q^1=7\text{-}NO_2$; R, $R_5=H$; m.p. 210°–212° C.

Compound 14: X, $X^1=H$; $X^2=8\text{-}CH_3O$; $Q=6\text{-}CH_3O$; $Q^1=7\text{-}CH_3O$; $Q^2=H$; R, $R_5=H$; m.p. 147°–149° C.

Compound 15: $X=6\text{-}CH_3O$; $X^1=7\text{-}CH_3O$; $X^2=H$; $Q=6\text{-}CH_3O$; $Q^1$, $Q^2=H$; R, $R_5=H$; m.p. 181°–184° C.

Compound 16: $X=6\text{-}CH_3O$; $X^1=7\text{-}CH_3O$; $X^2=H$; $Q=5\text{-}CH_3O$; $Q^1=6\text{-}CH_3O$; $Q^2=7\text{-}CH_3O$; R, $R_5=H$; m.p. 152°–153° C.

Compound 17: $X=6\text{-}CH_3O$; $X^1=7\text{-}CH_3O$; $X^2=H$; $Q=5\text{-}CH_3O$; $Q^1$, $Q^2=H$; R, $R_5=H$; m.p. 144.5°–146° C.

Compound 18: $X=6\text{-}CH_3O$; $X^1=7\text{-}CH_3O$; $X^2=H$; $Q=7\text{-}NH_2$; $Q^1$, $Q^2=H$; R, $R_5=H$; m.p. 123°–126° C.

Compound 19: $X=6\text{-}CH_3O$; $X^1=7\text{-}CH_3O$; $X^2=H$; $Q=7\text{-}Cl$; $Q^1$, $Q^2=H$; R, $R_5=H$; m.p. 187°–189° C.

Compound 20: $X=6\text{-}CH_3O$; $X^1=7\text{-}CH_3O$; $X^2=H$; $Q=6\text{-}CH_3O$; $Q^1=7\text{-}CH_3O$; $Q^2=8\text{-}CH_3O$; $R=C_2H_5O$; $R_5=H$; m.p. 150°–153° C.

Compound 21: $X=6\text{-}CH_3O$; $X^1=7\text{-}CH_3O$; $X^2=H$; $Q=H$; $Q^1=7\text{-}CH_3O$; $Q^2=8\text{-}CH_3O$; $R=CH_3O$; $R_5=H$; m.p. 138°–140° C.

Compound 22: $X=6\text{-}CH_3O$; $X^1=7\text{-}CH_3O$; $X^2=H$; $Q=6\text{-}CH_3O$; $Q^1$, $Q^2=H$; $R=C_2H_5O$; $R_5=H$; m.p. 140°–142° C.

Compound 23: $X=6\text{-}CH_3O$; $X^1=7\text{-}CH_3O$; $X^2=H$; $Q=H$; $Q^1=7\text{-}CH_3O$; $Q^2=8\text{-}CH_3O$; $R=C_2H_5O$; $R_5=H$; m.p. 161°–164° C.

Compound 24: $X=6\text{-}CH_3O$; $X^1=7\text{-}CH_3O$; $X^2=H$; $Q=6\text{-}CH_3O$; $Q^1=H$; $Q^2=8\text{-}CH_3O$; R, $R_5=H$; m.p. 159°–161° C.

Compound 25: $X=H$; $X^1=7\text{-}CH_3O$; $X^2=8\text{-}CH_3O$; $Q=6\text{-}CH_3O$; $Q^1=7\text{-}CH_3O$; $Q^2=H$; R, $R_5=H$; m.p. 143°–143.5° C.

Compound 26: $X=6\text{-}CH_3O$; $X^1=7\text{-}CH_3O$; $X^2=H$; $Q=6\text{-}CH_3O$; $Q^1=7\text{-}CH_3O$; $Q^2=8\text{-}CH_3O$; R, $R_5=H$; m.p. 152°–153° C.

Compound 27: $X=6\text{-}CH_3O$; $X^1=7\text{-}CH_3O$; $X^2=H$; $Q=7\text{-}CH_3$; $Q^1$, $Q^2=H$; R, $R_5=H$; m.p. 169°–170° C.

Compound 28: $X=5\text{-}Cl$; $X^1$, $X^2=H$; $Q=6\text{-}CH_3O$; $Q^1=7\text{-}CH_3O$; $Q^2=H$; R, $R_5=H$; m.p. 161°–162° C.

Compound 29: $X=6\text{-}Cl$; $X^1$, $X^2=H$; $Q=6\text{-}CH_3O$; $Q^1=7\text{-}CH_3O$; $Q^2=H$; R, $R_5=H$; m.p. 144°–145° C.

Compound 30: $X=6\text{-}CH_3O$; $X^1=7\text{-}CH_3O$; $X^2=H$; $Q=5\text{-}CH_3O$; $Q^1=6\text{-}CH_3O$; $Q^2=H$; R, $R_5=H$; m.p. 138.5°–139° C.

Compound 31: $X=6\text{-}CH_3O$; $X^1=7\text{-}CH_3O$; $X^2=H$; $Q=5\text{-}OH$; $Q^1=6\text{-}CH_3O$; $Q^2=H$; R, $R_5=H$; m.p. 221°–223° C.

Compound 32: $X=5\text{-}CH_3$; $X^1$, $X^2=H$; $Q=6\text{-}CH_3O$; $Q^1=7\text{-}CH_3O$; $Q^2=H$; R, $R_5=H$; m.p. 174°–175° C.

Compound 33: $X=6\text{-}CH_3O$; $X^1=7\text{-}CH_3O$; $X^2=H$; $Q=H$; $Q^1=7\text{-}CH_3O$; $Q^2=8\text{-}CH_3O$; $R=CH_3O$; $R_5=H$; m.p. 138°–140° C.

Compound 34: $X=6\text{-}CH_3O$; $X^1=7\text{-}CH_3O$; $X^2=H$; Q, $Q^1=H$; $Q^2=8\text{-}CH_3O$; R, $R_5=H$; m.p. 204°–205° C.

Compound 35: $X=6\text{-}CH_3O$; $X^1=7\text{-}CH_3O$; $X^2=H$; Q, $Q^1$, $Q^2=H$; $R=CH_3O$; $R_5=H$; m.p. 162°–165° C.

Compound 36: $X=6\text{-}CH_3O$; $X^1=7\text{-}CH_3O$; $X^2=H$; $Q=6\text{-}F$; $Q^1$, $Q^2=H$; $R=CH_3O$; $R_5=H$; m.p. 155°–157° C.

Compound 37: $X=6N(CH_3)_2$; $X^1$, $X^2=H$; $Q=6\text{-}CH_3O$; $Q^1=7\text{-}CH_3O$; $Q^2=H$; R, $R_5=H$; amorphous.

Compound 38: $X=6\text{-}CH_3O$; $X^1=7\text{-}CH_3O$; $X^2=H$; $Q=6\text{-}F$; $Q^1$, $Q^2=H$; $R=CH_3O$; $R_5=H$; m.p. 195°–197° C.

PREPARATION B

The procedure of Example 1A was repeated starting with the required materials to give the following intermediates:

[Structure diagram showing a phenyl ring with X, X¹, X² substituents bearing a C(=N–C(Cl)=N)–N(R₁)(R₂) group]

Compound 39: $X=6\text{-}CH_3O$; $X^1=7\text{-}CH_3O$; $X^2=H$;

$R_1R_2N = $ [indole-tetrahydropyridine structure];

m.p. 241°–243° C.
Compound 40: X=6-CH3O; X¹=7-CH3O; X²=H;

$R_1R_2N = C_2H_5O(CH_2)_2O-$ [piperidine] $N-$;

m.p. 91°–94° C.
Compound 41: X=6-CH3O; X¹=7-CH3O; X²=H;

$R_1R_2N = $ [pyridine]$-CH_2O-$[piperidine]$N-$ m.p. 149°–150° C.
Compound 42: X=6-CH3O; X¹=7-CH3O; X²=H;

$R_1R_2N = $ [benzoxazole-piperidine] $N-$;

Compound 43: X=6-CH3O; X¹=7-CH3O; X²=H;

$R_1R_2N = $ [benzazepine] $N-$;

m.p. 174°–176° C.
Compound 44: X=6-CH3O; X¹=7-CH3O; X²=H;

$R_1R_2N = $ [amino-benzazepine with H2N substituent];

m.p. 300° C.
Compound 45: X=6-CH3O; X¹=7-CH3O; X²=H;

$R_1R_2N = $ [benzodioxan-CH2NH];

m.p. 115°–119° C.
Compound 46: X, X¹, X²=H, R1R2N=C6H11NH;
m.p. 85°–89° C.

We claim:
1. A compound of the formula

[structure with X, X¹, X², R1, R2, R3, R4 substituents]

and pharmaceutically acceptable acid addition salts thereof wherein X and X¹ are each hydrogen, alkyl having one to four carbon atoms, alkoxy having one to four carbon atoms, bromo, iodo, nitro, amino, alkylamino having one to three carbon atoms, $(CH_3)_2S^{\oplus}$, aminomethyl, methylsulfinyl, dialkylaminomethyl having three to seven carbon atoms, methylthio, hydroxymethyl, benzoylamino, substituted benzoylamino wherein said substituent is azido, methoxy, methyl, fluoro, chloro or trifluoromethyl, alkanoylamino having two to four carbon atoms, 4-methylpiperazino, morpholino, thiomorpholino, piperazino, piperidino, pyrrolidino, dialkylamino having two to six carbon atoms, fluoro or chloro; X² is hydrogen, alkyl having one to four carbon atoms or alkoxy having one to four carbon atoms; or X and X¹ together are ethylenedioxy or methylenedioxy; R1 is alkoxyalkyl said alkoxy having from one to three carbon atoms and said alkyl having two to three carbon atoms, cycloalkyl having three to seven carbon atoms, alkyl having one to four carbon atoms or benzodioxan-2-ylmethyl; R2 is hydrogen, alkyl having one to eight carbon atoms or benzyl; or R1 and R2 when taken together with the nitrogen atom to which they are attached form (a) a moiety of the formula

[tetrahydroisoquinoline structure with Q, Q¹, Q², R, R5 substituents]

wherein Q is hydrogen, alkoxy having one to three carbon atoms, hydroxy, alkanoylamino having two to four carbon atoms, alkyl having one to three carbon atoms, bromo, iodo, fluoro, chloro, nitro, morpholino, amino, alkylamino having one to three carbon atoms or dialkylamino having two to six carbon atoms, Q¹ is hydrogen, fluoro, chloro, bromo, alkyl having one to three carbon atoms or alkoxy having one to three carbon atoms and Q² is hydrogen or alkoxy having one to three carbon atoms, or Q¹ and Q² together are ethylenedioxy or methylenedioxy, R is hydrogen, alkyl having one to four carbon atoms or alkoxy having one to three carbon atoms, R5 is hydrogen or dialkoxybenzyl said alkoxy having one to three carbon atoms or R and R5 together are alkylene having one to three carbon atoms, (b) 1,2,3,4-tetrahydro-beta-carbol-2-yl,
(c) piperidino of the formula

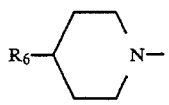

wherein R$_6$ is pyridylmethoxy, alkoxyalkyleneoxy said alkoxy having from one to three carbon atoms and said alkylene having from two to three carbon atoms or benzoxazol-2-ylmethyl,
(d) octahydroisoindol-2-yl or
(e) decahydroisoquinol-2-yl;
R$_3$ is
(a) cycloalkyl having three to seven carbon atoms,
(b) benzodioxan-2-ylmethyl,
(c) aralkyl of the formula

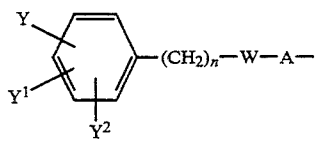

wherein n is an integer of 1 or 0, W is O, S or a chemical bond, A is alkylene having one to four carbon atoms, Y is hydrogen, alkyl having one to three carbon atoms, alkoxy having one to three carbon atoms, fluoro, chloro, bromo, hydroxy, benzyloxy, nitro, dimethylamino or amino, Y$^1$ is hydrogen, alkoxy having one to three carbon atoms, chloro, fluoro, hydroxy or benzyloxy, Y$^2$ is hydrogen or alkoxy having one to three carbon atoms or Y and Y$^1$ together are ethylenedioxy or methylenedioxy,
(d) aralkyl of the formula

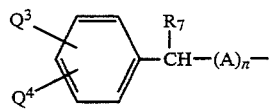

wherein R$_7$ is hydroxy, alkoxy having one to three carbon atoms or C$_6$H$_5$(CH$_2$)$_r$—, n is 1, t is an integer of 0 or 1, A is alkylene having one to four carbon atoms, Q$^3$ and Q$^4$ are each hydrogen or alkoxy having one to three carbon atoms or Q$^3$ and Q$^4$ together are ethylenedioxy or methylenedioxy;
(e) pyridylalkyl said alkyl having from one to four carbon atoms,
(f) alkoxyalkyl said alkoxy having from one to three carbon atoms and said alkyl having two to three carbon atoms,
(g) indolylalkyl of the formula

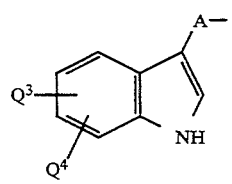

wherein A is alkylene having one to four carbon atoms, Q$^3$ and Q$^4$ are each hydrogen or alkoxy having one to three carbon atoms or Q$^3$ and Q$^4$ together are ethylenedioxy or methylenedioxy, (h) tetrahydronaphthalene of the formula

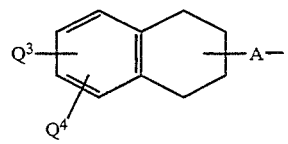

wherein A is alkylene having one to four carbon atoms, Q$^3$ and Q$^4$ are each hydrogen or alkoxy having one to three carbon atoms or Q$^3$ and Q$^4$ together are ethylenedioxy or methylenedioxy,
(i) aralkanol of the formula

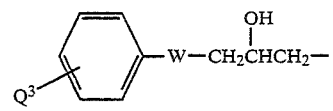

wherein W is O, S or a chemical bond and Q$^3$ is hydrogen or alkoxy having one to three carbon atoms,
(j) 2,3-dihydro-2-hydroxyinden-1-yl,
(k) aracycloalkyl of the formula

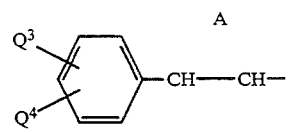

wherein A is alkylene having one to four carbon atoms, Q$^3$ and Q$^4$ are each hydrogen or alkoxy having one to three carbon atoms or Q$^3$ and Q$^4$ together are ethylenedioxy or methylenedioxy,
(l) indene of the formula

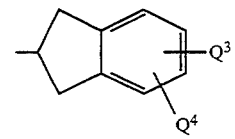

wherein Q$^3$ and Q$^4$ are each hydrogen or alkoxy having one to three carbon atoms or Q$^3$ and Q$^4$ together are ethylenedioxy or methylenedioxy,
(m) naphthyl or
(n) 1-methylpyrrol-2-yl;
R$_4$ is hydrogen or alkyl having one to eight carbon atoms, or R$_3$ and R$_4$ when taken together with the nitrogen atom to which they are attached form
(a) a tetrahydro isoquinoline of the formula

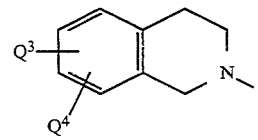

wherein Q$^3$ and Q$^4$ are each hydrogen or alkoxy having one to three carbon atoms or Q$^3$ and Q$^4$ together are ethylenedioxy or methylenedioxy,
(b) piperidino of the formula

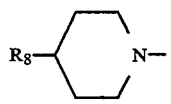

wherein $R_8$ is benzyl, alkoxyalkyleneoxy said alkoxy having from one to three carbon atoms and said alkylene having two to three carbon atoms or alkyl sulfonamide of the formula

wherein $R_9$ is alkyl having from one to four carbon atoms,
(c) 3-methyl-3-phenylpiperidino or
(d) piperazino of the formula

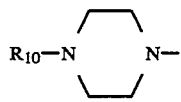

wherein $R_{10}$ is hydrogen, alkoxycarbonyl having from two to six carbon atoms, acyl having one to six carbon atoms, hydroxyalkoxy carbonyl having three to six carbon atoms, furoyl, benzoxazol-2-yl, pyrimid-2-yl or benzodioxan-2-carbonyl, provided that at least $R_1$ and $R_2$ are taken with the nitrogen atom to which they are attached to form a ring as defined hereinabove or $R_3$ and $R_4$ are taken with the nitrogen atom to which they are attached to form a ring as defined hereinabove and provided further that when X, $X^1$ and $X^2$ are each hydrogen;
or X and $X^1$ are each hydrogen and $X^2$ is alkyl having one to three carbon atoms;
or X and $X^2$ are each hydrogen and $X^1$ is alkyl having one to three carbon atoms, iodo, bromo, chloro or fluoro;
or $X^1$ and $X^2$ are each hydrogen and X is alkyl having one to three carbon atoms, iodo, bromo, chloro or fluoro;
$R_1$ is cycloalkyl having three to seven carbon atoms or alkyl having one to four carbon atoms;
$R_2$ is hydrogen or alkyl having one to six carbon atoms; or $R_1$ and $R_2$ when taken together with the nitrogen atom to which they are attached form octahydroisoindol-2-yl or decahydroisoquinol-2-yl; and
$R_3$ is cycloalkyl having three to seven carbon atoms;
then $R_4$ cannot be hydrogen or alkyl having one to six carbon atoms;
or $R_3$ and $R_4$ when taken together with the nitrogen atom to which they are attached cannot form piperazin-1-yl.

2. A compound of claim 1, wherein X and $X^1$ are each alkoxy having one to four carbon atoms, $X^2$ is hydrogen, $R_1$ and $R_2$ are taken together with the nitrogen atom to which they are attached form a moiety of the formula

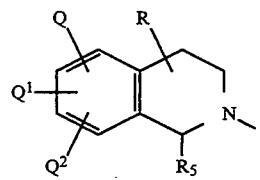

wherein $Q^1$ is alkoxy having one to three carbon atoms, R and $R_5$ are each hydrogen, $R_3$ is aralkyl of the formula

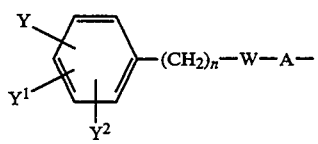

wherein $Y^1$ and $Y^2$ are each methoxy, n is 0, W is a chemical bond and A is ethylene and $R_4$ is hydrogen.

3. The compound of claim 2, wherein X is 6-methoxy, $X^1$ is 7-methoxy, Q is 5-hydroxy, $Q^1$ is 6-methoxy, $Q^2$ is hydrogen, Y is hydrogen, $Y^1$ is 2-methoxy and $Y^2$ is 3-methoxy.

4. The compound of claim 2, wherein X is 6-methoxy, $X^1$ is 7-methoxy, Q is 7-methoxy, $Q^1$ is 8-methoxy, $Q^2$ is hydrogen, Y is hydrogen, $Y^1$ is 3-methoxy and $Y^2$ is 4-methoxy.

5. The compound of claim 2, wherein X is 6-methoxy, $X^1$ is 7-methoxy, Q is 7-methoxy, $Q^1$ is 8-methoxy, $Q^2$ is hydrogen, Y is hydrogen, $Y^1$ is 2-methoxy and $Y^2$ is 3-methoxy.

6. The compound of claim 2, wherein X is 6-methoxy, $X^1$ is 7-methoxy, Q and $Q^2$ are each hydrogen, $Q^1$ is 6-methoxy, Y is hydrogen, $Y^1$ is 3-methoxy and $Y^2$ is 4-methoxy.

7. The compound of claim 2, wherein X is 6-methoxy, $X^1$ is 7-methoxy, Q is 5-methoxy, $Q^1$ is 6-methoxy, $Q^2$ is hydrogen, Y is hydrogen, $Y^1$ is 3-methoxy and $Y^2$ is 4-methoxy.

8. The compound of claim 2, wherein X is 6-methoxy, $X^1$ is 7-methoxy, Q is 6-methoxy, $Q^1$ is 7-methoxy, $Q^2$ is hydrogen, Y is 2-bromo, $Y^1$ is 4-methoxy and $Y^2$ is 5-methoxy.

9. The compound of claim 2, wherein X is 6-methoxy, $X^1$ is 7-methoxy, Q is 6-methoxy, $Q^1$ is 8-methoxy, $Q^2$ is hydrogen, Y is hydrogen, $Y^1$ is 3-methoxy and $Y^2$ is 4-methoxy.

10. The compound of claim 2, wherein X is 6-methoxy, $X^1$ is 7-methoxy, Q is 6-methoxy, $Q^1$ is 7-methoxy, $Q^2$ is hydrogen, Y is hydrogen, $Y^1$ is 3-methoxy and $Y^2$ is 4-methoxy.

11. A compound of claim 1, wherein $X^1$ and $X^2$ are each hydrogen, $R_1$ and $R_2$ are taken together with the nitrogen atom to which they are attached form a moiety of the formula

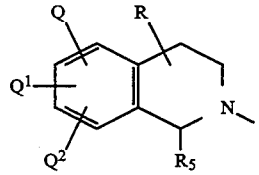

wherein Q and Q¹ are each alkoxy having one to three carbon atoms, Q² is hydrogen, R and R₅ are each hydrogen, R₃ is aralkyl of the formula

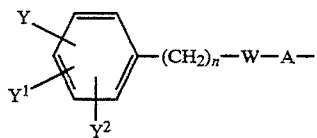

wherein Y² is hydrogen, n is 0, W is a chemical bond and A is ethylene and R₄ is hydrogen.

12. The compound of claim 11, wherein X is 5-methoxy, Q is 6-methoxy, Q¹ is 7-methoxy, Y is 2-chloro and Y¹ is hydrogen.

13. The compound of claim 11, wherein X is 5-chloro, Q is 6-methoxy, Q¹ 7-methoxy, Y is 2-chloro and Y¹ is hydrogen.

14. The compound of claim 11, wherein X is 5-methyl, Q is 6-methoxy, Q¹ is 7-methoxy, Y is 3-methoxy and Y¹ is 4-methoxy.

15. The compound of claim 11, wherein X is 6-dimethylamino, Q is 6-methoxy, Q¹ is 7-methoxy, Y is 3-methoxy and Y¹ is 4-methoxy.

16. A compound of claim 1, wherein X and X¹ are each alkoxy having one to four carbon atoms, X² is hydrogen, R₁ and R₂ are taken together with the nitrogen atom to which they are attached form a moiety of the formula

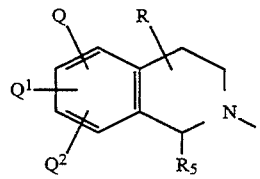

wherein Q² is hydrogen, R₅ is hydrogen, R₃ is aralkyl of the formula

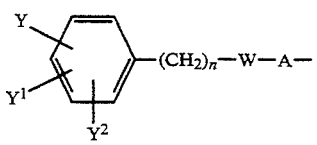

wherein Y and Y¹ are each alkoxy having one to three carbon atoms, Y² is hydrogen, n is 0, W is a chemical bond, A is ethylene and R₄ is hydrogen.

17. The compound of claim 16, wherein X is 6-methoxy, X¹ is 7-methoxy, Q and Q¹ are each hydrogen, R is methoxy, Y is 2-methoxy and Y¹ is 3-methoxy.

18. A compound of claim 1, wherein X and X¹ are each alkoxy having one to four carbon atoms, X² is hydrogen, R₁ and R₂ are taken together with the nitrogen atom to which they are attached form a moiety of the formula

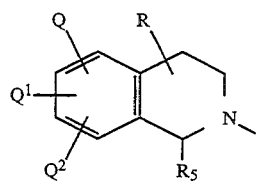

wherein Q and Q¹ are each alkoxy having one to three carbon atoms, Q² is hydrogen, R and R₅ are each hydrogen, R₃ is aralkyl of the formula

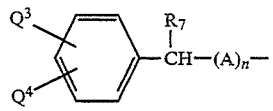

wherein Q³ and Q⁴ are each alkoxy having one to three carbon atoms, R₇ is methoxy, n is 1, A is methylene and R₄ is hydrogen.

19. The compound of claim 16, wherein X is 6-methoxy, X¹ is 7-methoxy, Q is 7-amino, Q¹ is hydrogen, R is hydrogen, Y is 3-methoxy and Y¹ is 4-methoxy.

20. A compound of claim 1, wherein X and X¹ are each alkoxy having from one to four carbon atoms, X² is hydrogen, R₁ and R₂ are taken together with the nitrogen atom to which they are attached form a moiety of the formula

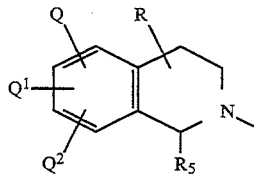

wherein Q¹ and Q² are each hydrogen, R₅ is hydrogen, R₃ is aralkyl of the formula

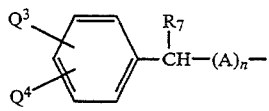

wherein Q³ and Q⁴ are each alkoxy having one to three carbon atoms, R₇ is methoxy, n is 1, A is methylene and R₄ is hydrogen.

21. The compound of claim 18, wherein X is 6-methoxy, X¹ is 7-methoxy, Q is 7-methoxy, Q¹ is 8-methoxy, Q³ is 2-methoxy and Q⁴ is 4-methoxy.

22. A compound of claim 1, wherein X¹ is alkoxy having one to four carbon atoms, X² is hydrogen, R₁ and R₂ are taken together with the nitrogen atom to which they are attached form a moiety of the formula

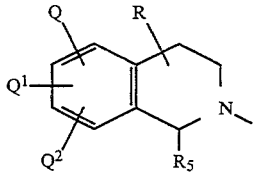

wherein Q and $Q^1$ are each alkoxy having one to three carbon atoms, $Q^2$ is hydrogen, $R_3$ is aralkyl of the formula

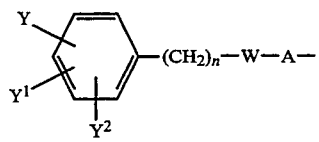

wherein $Y^2$ is hydrogen, n is 0, W is a chemical bond, A is ethylene and $R_4$ is hydrogen.

23. The compound of claim 20, wherein X is 6-methoxy, $X^1$ is 7-methoxy, Q is 6-fluoro, R is methoxy, $Q^3$ is 2-methoxy and $Q^4$ is 3-methoxy.

24. A pharmaceutical composition for administration to a mammal which comprises a P-glycoprotein inhibiting amount of a compound of claim 1, a pharmaceutically acceptable carrier and, optionally, an anticancer effective amount of a chemotherapeutic agent.

25. The compound of claim 22, wherein X is 6-chloro, $X^1$ is 7-methoxy, Q is 6-methoxy, $Q^1$ is 7-methoxy, R and $R_5$ are each hydrogen, Y is 3-methoxy and $Y^1$ is 4-methoxy.

26. A method of inhibiting a P-glycoprotein in a mammal in need of such treatment which comprises administering to said mammal a P-glycoprotein inhibiting amount of a compound according to claim 1.

27. A method of claim 1, wherein the mammal is a human suffering from cancer and said compound is administered before, with or after the administration to said human of an anticancer effective amount of a chemotherapeutic agent.

* * * * *